(12) United States Patent  
Atalla

(10) Patent No.: US 9,187,571 B2  
(45) Date of Patent: Nov. 17, 2015

(54) NANO-DEAGGREGATED CELLULOSE

(75) Inventor: Rajai H. Atalla, Verona, WI (US)

(73) Assignee: CELLULOSE SCIENCES INTERNATIONAL, INC., Verona, WI (US)

( * ) Notice: Subject to any disclaimer, the term of this patent is extended or adjusted under 35 U.S.C. 154(b) by 47 days.

(21) Appl. No.: 13/822,190

(22) PCT Filed: Sep. 14, 2011

(86) PCT No.: PCT/US2011/051592  
§ 371 (c)(1),  
(2), (4) Date: Mar. 11, 2013

(87) PCT Pub. No.: WO2012/037250  
PCT Pub. Date: Mar. 22, 2012

(65) Prior Publication Data  
US 2013/0172544 A1 Jul. 4, 2013

Related U.S. Application Data

(63) Continuation-in-part of application No. 12/935,447, filed as application No. PCT/US2009/039445 on Apr. 3, 2009.

(60) Provisional application No. 61/382,604, filed on Sep. 14, 2010, provisional application No. 61/042,133, filed on Apr. 3, 2008.

(51) Int. Cl.  
*D21H 11/18* (2006.01)  
*D21H 11/20* (2006.01)  
(Continued)

(52) U.S. Cl.  
CPC . *C08B 1/00* (2013.01); *C08B 15/08* (2013.01); *C08L 1/02* (2013.01); *C12P 19/14* (2013.01); *D21C 5/005* (2013.01); *D21H 17/005* (2013.01)

(58) Field of Classification Search  
CPC ............ D21C 5/00; D21C 9/00; D21C 9/001; D21C 9/002; D21C 9/007; D21H 11/00; D21H 11/18; D21H 11/20; C08B 15/00; C08B 15/02; C08B 15/08; C08B 16/00; C08L 1/00; C08L 1/02; C08L 1/04; C21P 19/14; C12P 19/14  
USPC ........... 162/146, 157.6, 9, 77, 90; 536/56, 57; 127/37  
See application file for complete search history.

(56) References Cited

U.S. PATENT DOCUMENTS 3,954,727 A * 5/1976 Toshkov et al. .................. 536/57  
4,100,016 A 7/1978 Diebold et al.  
(Continued)

FOREIGN PATENT DOCUMENTS

| EA | 006944 | 6/2006 |
| RU | 2158763 | 11/2000 |
| WO | WO 2006/002419 | 1/2006 |
| WO | WO 2007/111605 | 10/2007 |
| WO | 2009/084492 | 7/2009 |

(Continued)

OTHER PUBLICATIONS

Chinese Patent Office Action for Application No. 201180047601.2 dated Jun. 16, 2014 (7 pages, with English translation).

(Continued)

*Primary Examiner* — Eric Hug  
(74) *Attorney, Agent, or Firm* — Michael Best & Friedrich LLP

(57) ABSTRACT

Disclosed are methods and systems for treating cellulose to make it more accessible for enzymatic or chemical modification. The invention includes treating cellulose with an alkali in an alcohol/water co-solvent system. The treatment decrystallizes or deaggregates the cellulosic material. The methods and systems increase the efficiency of enzymatic or chemical modifications of cellulose for use as biofuels or cellulose derivatives.

12 Claims, 24 Drawing Sheets

X-ray diffractograms of bleached kraft pulp before and after decrystallization treatment.

(51) Int. Cl.
| | |
|---|---|
| *D21C 5/00* | (2006.01) |
| *C08B 15/08* | (2006.01) |
| *C08L 1/02* | (2006.01) |
| *C08B 1/00* | (2006.01) |
| *D21H 17/00* | (2006.01) |
| *C12P 19/14* | (2006.01) |

(56) References Cited

U.S. PATENT DOCUMENTS

| | | | |
|---|---|---|---|
| 4,395,543 | A | 7/1983 | Wang et al. |
| 4,880,473 | A | 11/1989 | Scott et al. |
| 5,503,709 | A | 4/1996 | Burton |
| 5,858,021 | A | 1/1999 | Sun et al. |
| 6,409,841 | B1 | 6/2002 | Lombard |
| 6,821,531 | B2 | 11/2004 | Kumar |
| 6,964,758 | B2 | 11/2005 | Cortright et al. |
| 7,005,514 | B2 | 2/2006 | Nguyen |
| 7,109,005 | B2 | 9/2006 | Eroma et al. |
| 7,396,434 | B2 | 7/2008 | Rodriguez Rivera et al. |
| 7,465,791 | B1 | 12/2008 | Hallberg et al. |
| 7,604,967 | B2 | 10/2009 | Yang et al. |
| 8,030,030 | B2 | 10/2011 | Varanasi et al. |
| 2002/0077328 | A1 | 6/2002 | Hassan et al. |
| 2002/0117276 | A1 | 8/2002 | Dorn et al. |
| 2003/0049707 | A1 | 3/2003 | Helbert et al. |
| 2003/0089465 | A1* | 5/2003 | Schaible et al. ............. 162/19 |
| 2003/0144245 | A1 | 7/2003 | Addis et al. |
| 2004/0074615 | A1 | 4/2004 | Nguyen |
| 2004/0226671 | A1 | 11/2004 | Nguyen et al. |
| 2005/0131255 | A1 | 6/2005 | Benderly et al. |
| 2005/0181485 | A1 | 8/2005 | Tsukamoto et al. |
| 2005/0272926 | A1 | 12/2005 | Lee et al. |
| 2005/0287208 | A1 | 12/2005 | Kumar et al. |
| 2006/0093672 | A1 | 5/2006 | Kumar et al. |
| 2006/0144535 | A1 | 7/2006 | Nguyen et al. |
| 2006/0154352 | A1 | 7/2006 | Foody et al. |
| 2006/0287517 | A1 | 12/2006 | Wang et al. |
| 2007/0031918 | A1 | 2/2007 | Dunson, Jr. et al. |
| 2007/0166805 | A1 | 7/2007 | Cosgrove et al. |
| 2008/0025903 | A1 | 1/2008 | Cortright |
| 2008/0057555 | A1 | 3/2008 | Nguyen |
| 2008/0060774 | A1 | 3/2008 | Zuraw et al. |
| 2008/0142176 | A1 | 6/2008 | van Heiningen et al. |
| 2008/0202504 | A1 | 8/2008 | Hilst |
| 2009/0017503 | A1 | 1/2009 | Zhang et al. |
| 2009/0061495 | A1 | 3/2009 | Beatty et al. |
| 2009/0221042 | A1 | 9/2009 | Dale et al. |
| 2010/0024810 | A1* | 2/2010 | Harmer et al. .................. 127/37 |
| 2010/0105891 | A1* | 4/2010 | Nojiri et al. .................... 536/124 |
| 2010/0143974 | A1 | 6/2010 | Chung et al. |
| 2010/0223839 | A1 | 9/2010 | Garcia-Perez et al. |
| 2010/0233771 | A1 | 9/2010 | McDonald et al. |
| 2010/0240112 | A1 | 9/2010 | Anttila et al. |
| 2011/0003341 | A1* | 1/2011 | Nojiri et al. ..................... 435/72 |
| 2011/0091940 | A1 | 4/2011 | Atalla |
| 2012/0103324 | A1* | 5/2012 | Osaki et al. ...................... 127/34 |
| 2013/0172544 | A1 | 7/2013 | Atalla |
| 2014/0220228 | A1 | 8/2014 | Atalla |

FOREIGN PATENT DOCUMENTS

| | | | |
|---|---|---|---|
| WO | WO 2009/084492 | * | 7/2009 |
| WO | WO 2009/124240 | | 10/2009 |
| WO | 2010/014503 | | 2/2010 |
| WO | WO 2012/027767 | | 3/2012 |
| WO | WO 2012/037250 | | 3/2012 |
| WO | WO 2012/109651 | | 8/2012 |

OTHER PUBLICATIONS

Jacquet et al., New ether-linked ferulic acid-coniferyl alcohol dimers identified in grass straws, 1995, Journal of Agricultural and Food Chemistry 43(1 0): 2746-2751.

Buranov et al., Extraction and purification of ferulic acid from flax shives, wheat and corn bran by alkaline hydrolysis and pressurised solvents, 2009, Food Chemistry 115(4): 1542-1548.

United States Patent Office Action for U.S. Appl. No. 14/143,817 dated Sep. 4, 2014 (15 pages).

Agarwal, U.P. et al., "Cellulose I crystallinity determination using FT-Raman spectroscopy: univariate and multivariate methods," Cellulose (2010) 17:721-733.

Atalla et al., "An innovative new technology to reduce recalcitrance of cellulose and make it competitive with corn as a biomass feedstock," (2009) 1-6, retrieved from the Internet: URL:celscint.com/uploads/CSI_Technology.pdf, retrieved on Aug. 24, 2009; XP-002542665.

Atalla, Atalla and Vanderhart, D.L., "Native cellulose: a composite of two distinct crystalline forms" Science, 223:283 (1984).

Atalla, R. H., Procedures for Reducing the Recalcitrance of Native Celluloses, Cellulose Sciences International, Jan. 7, 2008 (5 pages).

Atalla, R.H. And Agarwal, U.P., "Raman microprobe evidence for lignin orientation in cell walls of native woody tissue" Science, 227:636 (1985).

Atalla, R.H. and Nagel, S.C., "Cellulose: Its regeneration in the native lattice" Science, 185:522 (1974).

Atalla, R.H. and Whitmore, R., "The influence of elevated temperatures of structure in the isolation of native cellulose," J. Polymer Sci. Polymer Lett. 16:601-605 (1978).

Atalla, Rajai H., "Reducing the Recalcitrance of Cellulose to Enhance its Utility as a Feedstockin the Production of Biofuels and Chemicals," SBIR Proposal, Funding Opportunity Number: DE-PS02-07ER07; CDFA Number: 81.049 (17 pages).

Bandura et al., The ionization constant of water over wide ranges of temperature and density, 2006, Journal of Physical and Chemical Reference Data 35(1 ): 15-30.

Dimick, Bruce E., "The Importance of the Structure of Alkali Metal Hydroxide Solutions in Decrystallizing Cellulose I," Dissertation, Institute of Paper Chemistry, Appleton, WI 1976.

Goho, Alexandra M., Better Bugs for Making Butanol, MIT Technology Review, 2008 (2 pages).

Gupta, Rajesh and Lee, Y. Y., Measurement of Endo and Exo-Glucanase Activities in Cellulase Using Non-Crystalline Cellulose, Chemical Engineering, Aubrun University, Auburn, AL 36849, 1 page, Nov. 16, 2006.

Isogai, I. et al., "Dissolution of cellulose in aqueous NaOH solutions," Cellulose (1998) 5:309-319; XP-002542664.

Isogai and Atalla, "Amorphous celluloses stable in aqueous media: Regeneration from SO2—amine solvent systems," Journal of Polymer Science: Polymer Chemistry, 29 (1991) pp. 113-119.

Jeffries, et al., "The Function of Swelling in the Finishing of Cotton" Textile Res, J., 39, 548 (1969).

Lee Jae-Won et al., "Biological Pretreatment of Softwood Pinus densiflora by Tree White Rot Fungi," The Journal of Microbiology, Dec. 2007, No. 6, pp. 485-491.

Pan, X. et al., "The bioconversion of mountain pine beetle-killed lodgepole pine to fuel ethanol using the organosols process," Biotech. Bioeng. (2008) 101(1):39-48; XP-002542737.

Park, S. et al., "Cellulose crystallinity index: measurement techniques and their impact on interpreting cellulase performance," Biotechnol. Biofuels (2010) 3:10.

Peri, Suma and Lee, Y.Y., "Kinetic Investigation of Cellulase Enzyme Using Non-Crystalline Cellulose and Cello-Oligosaccharides," Poster Presentation 1B-60, Auburn University, AL 36849, 1 page.

Peri, Suma and Lee, Y. Y., "Kinetic Investigation and Modeling of Cellulase Enzyme Using Non-Crsytalline Cellulose and Cello-Oligosaccharides," Thesis submitted to Auburn University, Aug. 7, 2006, 99 pages.

Pu, Y. et al., "The new forestry biofuels sector," Biofuels, Bioproducts & Biorefining (2007) 2:58-73; XP-002542739.

SBIR Phase I Grant No. 99031, "Overcoming the Recalcitrance of Cellulose" (2010).

Schroeder, LeLand R. et al., Nondegradative Preparation of Amorphous Cellulose, The Institute of Paper Chemistry, Appleton, WI 54912, Mar. 1985 (15 pages).

(56) References Cited

OTHER PUBLICATIONS

Smith, Bronwen et al., Crystalline Cellulose in Hydrated Primary Cell Walls of Three Monocotyledons and One Dicotyledon, Plant and Cell Physiology, 1998, vol. 39, No. 7, 711-720.

Sun, X-F. et al., "Comparative study of crude and purified cellulose from wheat straw," J. Agricul. Food Chem. (2004) 52:839-847; XP-002542740.

U.S. Department of Energy, "Breaking the Biological Barriers to Cellulosic Ethanol: A Joint Research Agenda" A Research Roadmap Resulting from the Biomass to Biofuels Workshop, Dec. 7-9, 2005, Rockville, Maryland: Jun. 2006; DOE/SC-0095.

Walseth, Curtis S., "Enzymatic Hydrolysis of Cellulose," Dissertation, Institute of Paper Chemistry, Appleton, WI 1948.

Zhao, Y. et al., "Enhanced enzymatic hydrolysis of spruce by alkaline pretreatment at low temperature," Biotech. Bioeng. (2007) 99(6):1320-1328; XP-002542738.

International Search Report and Written Opinion for Application No. PCT/US2009/039445 dated Sep. 10, 2009 (10 pages).

Invitation to Pay Additional Fees and, Where Applicable, Protest Fee for Application No. PCT/US2011/51592 dated Jan. 23, 2012 (3 pages).

International Search Report and Written Opinion for Application No. PCT/US2011/51592 dated Mar. 28, 2012 (14 pages).

International Preliminary Report on Patentability for Application No. PCT/US2011/51592 dated Mar. 19, 2013 (10 pages).

International Search Report and Written Opinion for Application No. PCT/US2012/024871 dated Aug. 2, 2012 (11 pages).

United States Patent Office Action for U.S. Appl. No. 12/935,447 dated May 23, 2012 (8 pages).

United States Patent Office Action for U.S. Appl. No. 12/935,447 dated Jul. 12, 2012 (15 pages).

United States Patent Office Final Rejection for U.S. Appl. No. 12/935,447 dated Mar. 14, 2013 (12 pages).

United States Patent Office Notice of Allowance for U.S. Appl. No. 12/935,447 dated Aug. 29, 2013 (12 pages).

European Extended Search Report for Application No. 11825870.6 dated Jan. 9, 2015 (6 pages).

\* cited by examiner

X-ray diffractograms of bleached kraft pulp before and after decrystallization treatment.

X-ray diffractograms of cellulose isolated from southern pine. (C) control pulped at 60°C, (A) Annealed heated up to 150°C in water.

Width at half-height of samples annealed at different temperatures

X-ray diffraction patterns of the original and modified native celluloses: (A) Whatman CF1, (B) ramie, (C) cotton, (D) algal cellulose.

X-ray diffraction patterns of celluloses regenerated from the SO$_3$-DEA-DMSO solvent system in water. These were prepared from: (A) Whatman CF1, (B) ramie, (C) cotton, (D) algal cellulose.

Avicel stained with Graff's C stain.

Avicel treated to create the novel state of aggregation stained with Graff's C stain

A  B

NANO-DEAGGREGATED CELLULOSE

CROSS-REFERENCE TO RELATED APPLICATIONS

This application claims the benefit under 35 U.S.C. §119(e) of U.S. Provisional Application No. 61/382,604, filed Sep. 14, 2010, the disclosure of which is incorporated herein by reference in its entirety.

STATEMENT REGARDING FEDERALLY SPONSORED RESEARCH OR DEVELOPMENT

Not Applicable.

INTRODUCTION

Cellulose is the most abundant of all naturally occurring polymers. Cellulose is the most common component of plant cell walls as it forms much of the structural framework of the cell wall. Chemically, it is a polysaccharide composed of anhydroglucose units (β-D glucopyranose rings) joined by an oxygen linkage (β-1,4-glycosidic linkage), and has the empirical formula $(C_6H_{10}O_5)_n$. It has a linear chain structure that forms crystalline nanofibrils in which many parallel β-1,4-glucan strands associate side by side to form nano-scale microfibrils (2-20 nm diameter and 100-40,000 nm long) that have great tensile strength and chemical stability, and are very resistant to breakdown, e.g., enzymatic, chemical and mechanical degradation. Cellulose is insoluble in water and simple organic solvents. It will swell in solutions of sodium hydroxide, and is soluble in Schweitzer's reagent.

Cellulose has been known to occur in different states of aggregation at the molecular level. Some are common and occur in commerce such as the native form, usually referred to as cellulose I, and the mercerized form or the regenerated form usually referred to as cellulose II. Other states of aggregation are known as well such as cellulose III produced by treatment with anhydrous ammonia or anhydrous amines, or cellulose IV usually prepared by heating celluloses II or III in glycerol at elevated temperatures. The latter two forms have generally been of academic interest and are not known to be of commercial utility. However, in all of these forms, the tightly aggregated domains have been regarded as crystalline with the molecular chains aligned parallel to each other and the individual anhydroglucose units making up the molecular chains organized in a specific pattern relative to each other.

Commercially, cellulose is used to make paper, plastics, and textiles. Cellulose derivatives include rayon, cellophane, thickeners used in foods and paints, and coatings. More recently, the biofuels industry has shown great interest in cellulosic feedstocks for producing biofuels, such as alcohols, e.g., ethanol or butanol, through microbiological processes, as well as hydrocarbons through chemical catalytic conversion.

The attractiveness of producing biofuels from cellulosic feedstocks, such as agricultural wastes, grasses, and forestry wastes, emanates from the availability of large amounts of these inexpensive feedstocks, and the desirability to avoid burning or landfilling cellulosic waste materials. Some cellulosic feedstocks that may be used for biofuels production specifically include (1) agricultural wastes, such as corn stover, wheat straw, barley straw, rice straw, oat straw, oat hulls, canola straw, and soybean stover; (2) grasses, such as switch grass, miscanthus, cord grass, and reed canary grass; (3) forestry wastes, such as aspen wood and sawdust; and (4) sugar processing residues, such as bagasse and beet pulp.

The conversion process of cellulosic fibers to a biofuel requires: 1) liberating cellulose and hemicellulose from lignin and/or increasing accessibility of cellulose and hemicellulose within the cellulosic feedstock to cellulase enzymes; and 2) depolymerizing or hydrolyzing hemicellulose and cellulose carbohydrate polymers to free sugars. To produce alcohols, the sugars are then fermented to an alcohol, e.g., ethanol, and the alcohol recovered, typically via distillation. Alternatively, the sugars can be converted to hydrocarbons through catalytic reformulation.

However, as noted above, cellulose contained in most plant matter is not readily convertible to sugars. Such conversion represents a major hurdle in the commercialization of processes for biofuels production. Because of the crystalline structure of cellulose, enzymatic conversion to sugars, for example, takes a considerable amount of time and requires large quantities of hydrolytic enzymes, such as cellulases. Likewise for the production of chemically-modified cellulose derivatives, cellulose must be made accessible to reactive chemical agents; this usually requires high temperature, pressures, harsh chemical conditions, and extended periods of time.

The efficient conversion of cellulose from cellulosic material into sugars was originally thought to simply involve liberating cellulose and hemicellulose from their complex with lignin. However, more recent processes focus on increasing the accessibility to cellulose within the lignocellulosic biomass followed by depolymerization or hydrolysis of cellulose carbohydrate polymers to sugars. Increasing the accessibility to cellulose is most often accomplished by pretreating the cellulosic substrate.

The goal of most pretreatment methods is to deliver a sufficient combination of mechanical and chemical action, so as to disrupt the fiber structure and improve the accessibility of the feedstock to hydrolytic enzymes, such as cellulases, which can hydrolyze cellulose. Mechanical action typically includes the use of pressure, grinding, milling, agitation, shredding, compression/expansion, or other types of mechanical action. Chemical action typically includes the use of heat (often steam), acid, and organic solvents.

Even with the most efficient of the currently known pretreatment processes, the amount of hydrolytic enzymes required to convert cellulose to sugars continues to be high and represents a significant cost in cellulosic biofuel production. Thus, the efficient conversion of cellulose from cellulosic material into sugars, and, for example, the subsequent fermentation of sugars to alcohol, such as ethanol, faces a major challenge for commercial viability. Increasing hydrolysis times to avoid higher costs of increasing enzyme dosage requires larger reactors, which, in turn, increases equipment costs. Mixing and intermittent mixing of the feedstock during hydrolysis can increase enzyme efficiency but equipment costs again increase, and increased shear forces can cause enzyme denaturation. Still other systems compromise the optimal enzyme activity and reduce the efficiency of the enzymes.

Furthermore, the difficulty with the conversion of cellulose to high value-added products extends well beyond biofuel production. As noted, cellulose derivatives include fibers and plastics, e.g., regenerated celluloses such as rayon and cellophane, cellulose esters such as acetate, butyrate, triacetate and mixed esters, cellulose nitrate, viscose, and lyocell (Tencel). Some of the cellulose crystalline domains are so tightly aggregated that chemical reagents cannot fully penetrate them, similar to lack of access for enzymes to hydrolyze them fully. The result is that the degree of substitution along the chains of cellulose in the cellulose derivatives can be quite irregular resulting in quality control problems.

BRIEF DESCRIPTION

According to the principles manifest in embodiments of the invention, methods and systems are provided which deaggregate, decrystallize or disorder cellulose so that it is more accessible for enzymatic or chemical modification, e.g., depolymerization or hydrolysis reactions. The methods and systems, in effect, enhance the conversion of cellulose-based feedstocks for use in production of biofuels and cellulose derivatives.

The methods and systems herein include treating cellulosic feedstocks with a solution of an alkali in a co-solvent system, e.g., water and a second solvent that is polar and fully water-miscible, to form a decrystallized/deaggregated cellulose, and stabilizing the decrystallized cellulose by washing out the alkali to yield a decrystallized/deaggregated cellulose in an aqueous medium. The washing may be accomplished with a co-solvent system that is the same as in the treating step with the varying ratios of water and second solvent. Among the most effective co-solvents identified so far are alcohols. In embodiments of the invention, this process is carried out under mild conditions of temperature and pressure.

Embodiments of the invention also provide a novel nano-deaggregated cellulose, a partially disordered form of aggregation that has not been previously reported. Nano-deaggregated cellulose can be formed from cellulose in one of the well-known states of aggregation, common in commerce, such as celluloses I and II. The latter are ordered states wherein the cellulose chain molecules as well as the anhydroglucose units are organized in well-established patterns as noted above. In nano-deaggregated cellulose, these chain molecules are separated in a manner that introduces significant internal disorder of the anhydroglucose units within individual chains while apparently maintaining the spatial relationship of the chain molecules relative to each other. That is, while it appears that the internal organization of individual chains is less ordered than it is in the cellulosic source material, after transformation to the nano-deaggregated cellulose, the molecular chains seem to retain their organization parallel to each other in a manner not unlike that prevailing in the source celluloses. Thus, while the known cellulosic substances retain their organization at both the macroscopic and microscopic levels, nano-deaggregated cellulose organization is altered at the nanoscale level. That is, the nano-deaggregated cellulose is a partiality-deaggregated cellulose at the nano scale. The alteration is such that the space between the molecular chains is increased. As a consequence of these changes in molecular organization, the macroscopic properties of the cellulosic substances are altered. The significance of these alterations is to allow a number of enhancements of the performance of celluloses in many traditional applications and allow consideration of a number of novel applications.

It is emphasized that the disorder developed within the celluloses possessing the novel state of aggregation in accordance with the invention is distinctly different from other known disordered or disaggregated celluloses produced by traditional methods. For example, it is known that amorphous celluloses can be prepared by ball-milling celluloses. Such ball-milled celluloses are homogeneously disordered, and upon wetting, they have been observed to aggregate in the cellulose II form. Other disordered celluloses can be regenerated from organic solvents in a truly amorphous state that is homogeneously disordered and where there is no memory of the native morphology of the source cellulose. In contrast, the nano-deaggregated cellulose in accordance with embodiments of the invention, is stable in water and aqueous media, and the native morphology of the source cellulose at the microscale and the macroscale are retained. The essential disorder is a partial one at the nanoscale.

BRIEF DESCRIPTION OF THE DRAWINGS

The invention may be better understood and appreciated by reference to the detailed description of specific embodiments presented herein in conjunction with the accompanying drawings of which.

DETAILED DESCRIPTION

Figure 1:
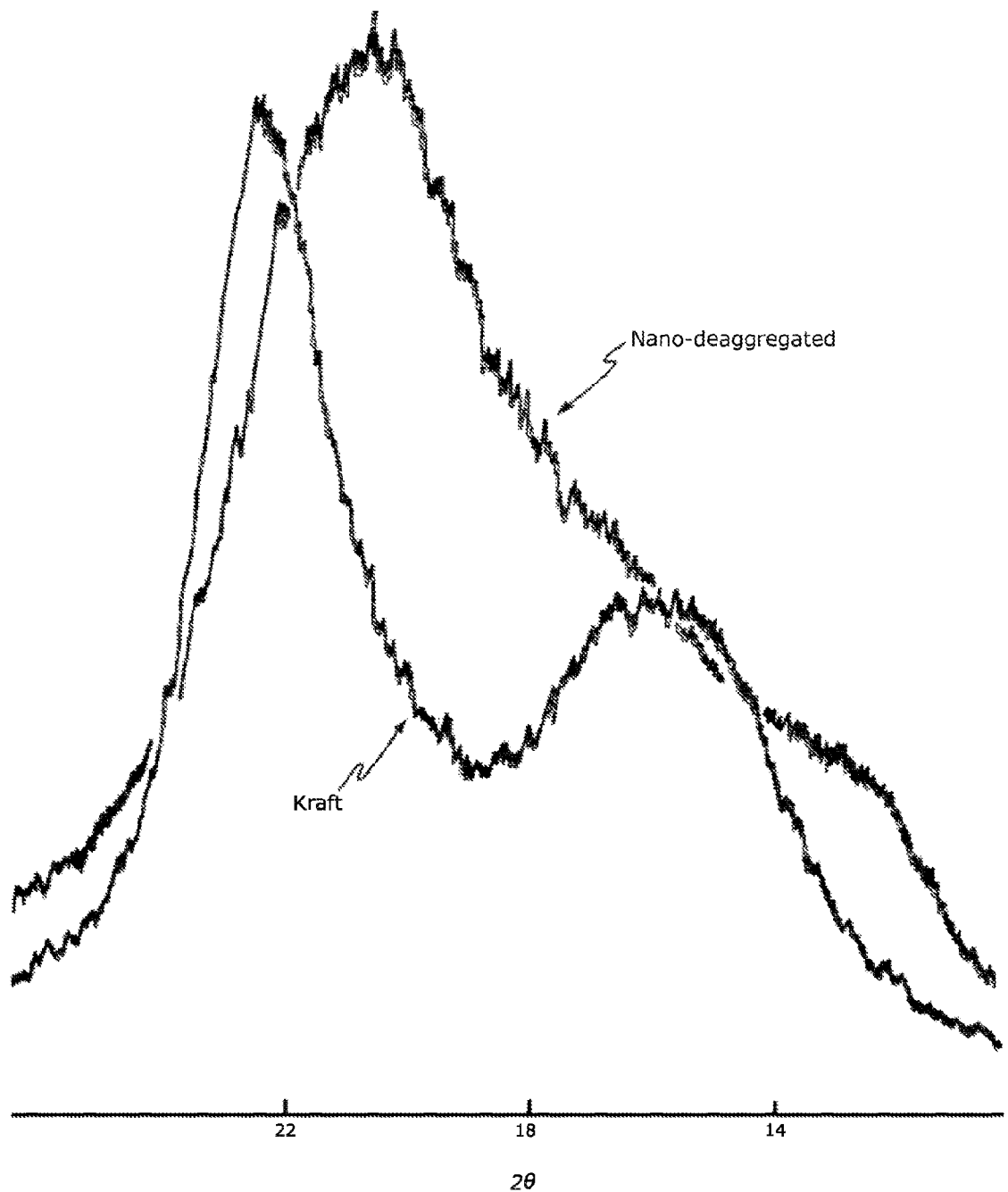
FIG. 1 is an x-ray diffractogram of a pulp before and after the pretreatment process in accordance with embodiments of the invention.

Methods and systems embodying the principles of the invention are provided in which cellulosic materials are decrystallized or nano-deaggregated by treatments which include contacting a cellulosic material with an alkali in a co-solvent system that includes water and a water-miscible solvent, e.g., an alcohol or polyol. The decrystallized/de-aggregated cellulose is more accessible for enzymatic and chemical reaction. The methods and systems in accordance with embodiments of the invention, thus, increase the efficiency of enzymatic or chemical modification of cellulose for use as biofuels or cellulose derivatives.

Before any embodiments of the invention are explained in detail, however, it is to be understood that the invention is not limited in its application to the details of construction and the arrangement of components set forth in the following description, illustrated in the following drawings or exemplified by the Examples. Such description, drawings, and Examples are not intended to limit the scope of the invention as set forth in the appended claims. The invention is capable of other embodiments and of being practiced or of being carried out in various ways.

Further, no admission is made that any reference, including any patent or patent document, cited in this specification constitutes prior art. In particular, it will be understood that, unless otherwise stated, reference to any document herein does not constitute an admission that any of these documents form part of the common general knowledge in the prior art in the United States or in any other country. Any discussion of the references states what their authors assert, and the applicant reserves the right to challenge the accuracy and pertinence of any of the documents cited herein.

Throughout this disclosure, various aspects of this invention may be presented in a range format. It should be understood that the description in range format is merely for convenience and brevity, and should not be construed as an inflexible limitation on the scope of the invention. Accordingly, as will be understood by one skilled in the art, for any and all purposes, particularly in terms of providing a written description, all ranges disclosed herein also encompass any and all possible subranges and combinations of subranges thereof, as well as all integral and fractional numerical values within that range. As only one example, a range of 20% to 40% can be broken down into ranges of 20% to 32.5% and 32.5% to 40%, 20% to 27.5% and 27.5% to 40%, etc. Any listed range is also easily recognized as sufficiently describing and enabling the same range being broken down into at least equal halves, thirds, quarters, fifths, tenths, etc. As a non-limiting example, each range discussed herein can be readily broken down into a lower third, middle third, and upper third, etc.

Further, as will also be understood by one skilled in the art, all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio. Further, the phrases "ranging/ranges between" a first indicate number and a second indicate number and "ranging/ranges from" a first indicate number "to" a second indicate number are used herein interchangeably. The foregoing are only examples of what is specifically intended.

Also, it is to be understood that the phraseology and terminology used herein is for the purpose of description and should not be regarded as limiting. The use of "comprising," "including," "having," and variations thereof herein is meant to encompass the items listed thereafter and equivalents thereof as well as additional items. "Comprising" encompasses the terms "consisting of" and "consisting essentially of." The use of "consisting essentially of" means that the composition or method may include additional ingredients and/or steps, but only if the additional ingredients and/or steps do not materially alter the basic and novel characteristics of the claimed composition or method.

Unless specified or limited otherwise, the terms such as "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Unless otherwise noted, technical terms are used according to conventional usage. However, as used herein, the following definitions may be useful in aiding the skilled practitioner in understanding the invention:

As used herein, the terms "cellulosic source material" or "cellulose starting material" is meant to refer to one of the known ordered forms of cellulose, e.g., cellulose I or cellulose II. Cellulosic source material may include one or more species of fiber that originate from different cellulosic feedstocks, especially straws, stover and bagasse and others listed below that have widespread availability and low cost.

The terms "cellulosic feedstock", "cellulosic substrate" or "cellulosic material" are also used and are meant to refer to any type of biomass that contains cellulose. For example, cellulosic feedstocks may include grasses such as switch grass, cord grass, rye grass, miscanthus, or a combination thereof; sugar-processing residues such as sugar cane bagasse and sugar beet pulp; agricultural wastes such as soybean stover, corn stover; oat straw, rice straw, rice hulls, barley straw, corn cobs, wheat straw, canola straw, oat hulls, and corn fiber; and forestry wastes, such as recycled wood pulp fiber, sawdust, hardwood, softwood, or any combination thereof. Further, the cellulosic feedstock may include cellulosic waste or forestry waste materials such as newsprint, cardboard and the like. Cellulosic feedstock may also include one or more species of fiber that originate from different cellulosic feedstocks. Wheat straw, barley straw, corn stover, soybean stover, canola straw, switch grass, reed canary grass, sugar cane bagasse, cord grass, oat hulls, sugar beet pulp and miscanthus are particularly advantageous as cellulosic feedstocks due to their widespread availability and low cost.

The term "hydrolytic enzyme(s)" is meant to refer to enzymes that catalyze hydrolysis of biological materials such as cellulose. Hydrolytic enzymes include "cellulase enzymes" or "cellulases" (used interchangeably) which are enzymes that catalyze the hydrolysis of cellulose to products such as glucose, cellobiose, cello-oligodextrins, and other cello-oligosaccharides. The reaction may also be referred to as "sacchrification." "Cellulase" is meant to be a generic term denoting a multienzyme complex or family, including exo-cellobiohydrolases (CBH), endoglucanases (EG), and β-glucosidases (βG) that can be produced by a number of plants and microorganisms. It is noted that many crude cellulase extracts also include some hemicellulases. The process in accordance with embodiments of the invention may be carried out with any type of cellulase enzyme complex, regardless of their source; however, microbial cellulases are generally available at lower cost than those of plants. Among the most widely studied, characterized, and commercially produced cellulases are, e.g., those obtained from fungi of the genera *Aspergillus, Humicola*, and *Trichoderma*, and from the bacteria of the genera *Bacillus* and *Thermobifida*. Also, for example, cellulase produced by the filamentous fungi

*Trichoderma longibrachiatum* includes at least two cellobiohydrolase enzymes termed CBHI and CBHII and at least 4 EG enzymes.

"Fermentation enzymes" refer to enzymes that can catalyze the conversion of the cellulosic sugars to alcohols, including ethanol as well as higher chain alcohols such as butanol.

Typically, yeast such as *Saccharomyces cerevisiae* is used to produce the enzymes that catalyze the conversion. Enzymes may also include bacterial enzymes from *Clostridium acetobuytlicum* as well as enzymes produced by engineered microorganisms to produce the higher chain alcohols from the sugars of cellulose.

The term "degree of polymerization" (abbreviated as D.P.) refers to the number of D-glucose monomers in a cellulose molecule. Thus, the term "average degree of polymerization", or "average D.P.", refers to the average number of D-glucose molecules per cellulose polymer in a population of cellulose polymers.

As used herein, the terms "treatment," "treating," "pretreatment," or "pretreating" in respect of cellulose are meant to refer to a process or treatment in accordance with embodiments of the invention in which cellulose is altered at the nanoscale to make it more accessible for enzymatic or chemical, e.g., chemical catalytic, reaction.

"Modification or degradation" in reference to cellulose is used to refer to the biological, e.g., enzymatic, or chemical-induced alteration of the native structure of cellulose. Such changes and alterations are known to those in the art and include those involved in enzymatic degradation and/or enzymatic or chemical hydrolysis of cellulose, as well as chemical modifications involved in a variety of commercial cellulose-based products, production of alcohols by fermentation of biomass, and generation of hydrogen-rich biofuels.

The term "stable" or "stabilizing" in regard to decrystallized/deaggregated cellulose refers to decrystallized cellulose that has altered molecular order at the nano-level and that does not change materially over a selected period of time and under selected conditions.

"Decrystallized cellulose", "disordered cellulose" and/or "nano-deaggregated cellulose" are used interchangeably and refer to a cellulose that, at the nano scale, is partially disordered or deaggregated, i.e., there is significant internal disorder of the anhydroglucose units within individual chains while apparently maintaining the generally parallel spatial relationship of the chain molecules relative to each other. These celluloses may also be referred to as "nano-deaggregated," "nano-decrystallized" or "nano-disordered" celluloses. That is, while it appears that the internal organization of individual chains is less ordered than it is in cellulosic source material, i.e., well-known ordered celluloses, after transformation to the nano-deaggregated cellulose, the molecular chains seem to retain their organization parallel to each other in a manner not unlike that prevailing in the source celluloses. While known cellulosic substances retain their organization at both the macroscopic and microscopic levels, in nano-deaggregated cellulose, the organization at the nanoscale level is altered. The alteration is such that the space between the molecular chains is increased. As a consequence of these changes in molecular organization, the macroscopic properties of the cellulosic substances are altered.

In view of the foregoing disadvantages inherent in conventional cellulose conversion, embodiments of the invention provide novel methods for decrystallizing or deaggregating cellulose. The methods include reacting cellulose with a treatment solution, which includes an alkali dissolved in a co-solvent system, under mild conditions of temperature and pressure that may be optimized for economic feasibility. Subjecting the cellulose to such treatment in accordance with embodiments of the invention makes the cellulose more accessible for enzymatic or chemical reaction, by opening up the tightly aggregated domains, which are also the source of recalcitrance during hydrolysis. The resulting decrystallized/deaggregated cellulose in accordance with embodiments of the invention also allows for much more uniform substitution along the cellulose chains, thus minimizing problems of quality control currently inherent in producing cellulose derivative products. Reference is made to FIG. 1, which shows an x-ray diffractogram of pulp before and after treatment in accordance with embodiments of the invention, demonstrating the decrystallization of the pulp.

There are many solvent systems that can swell native celluloses without solubilizing them. With the process in accordance with embodiments of the invention that opens up the semicrystalline cellulose domains, it is likely that a number of the systems that swell cellulose can be used to solubilize it, and thus, make possible cellulose regeneration in an economically competitive process.

As described above, the treatment solution in accordance with embodiments of the invention includes an alkali dissolved in a co-solvent system. Suitably, the alkali is dissolved in a co-solvent system of water plus a second water-miscible solvent. In one aspect, the second solvent is suitably an alcohol which may include, e.g., methanol, ethanol, propanol, isopropanol, butanol, isobutanol, or a polyol. In another aspect, the second solvent may include other protic solvents as well as aprotic solvents that are miscible in water. In an illustrated embodiment, the co-solvent system is ethanol and water.

In some embodiments of the invention, the alkali is suitably sodium hydroxide (NaOH), although other alkalis may be used, such as lithium hydroxide (LiOH) or potassium hydroxide (KOH). The concentration of NaOH needed in the treatment solution depends on the nature of the cellulose to be treated, as different celluloses may have their lattice forms disrupted at different concentrations of alkali. For example, the threshold for mercerization of most pulps is approximately 8% NaOH in water; for cotton, it is about 11 to 12%, depending on prior pretreatment; and for bacterial cellulose, it is about 14%.

Establishing the molarity of NaOH of the treatment solution is an iterative process. As a beginning point, the co-solvent ratio is fixed at a level that was found optimal in the finishing of cotton (4), which is reported to be 75% ethanol and 25% water. The molarity is then varied and the effectiveness of the treatment is assessed until an optimum molarity of the NaOH in the co-solvents is identified.

In some Examples below, the effect of the solutions on Avicel, a microcrystalline cellulose prepared from northern softwood (American Viscose Company, Marcus Hook, Pa.) and pulped at 180° C., was compared with earlier observations on other celluloses. It was found that a molarity of NaOH solutions between 1 M and 2 M worked well. Avicel was selected for the testing because it has become the standard substrate used in most published studies of bioconversion of cellulose. Avicel is a highly recalcitrant cellulose and representative of the effects of elevated temperature on pulp crystallinity. In additional Examples, kraft pulps derived from a toilet paper were used. The toilet paper was of the type designed for use in septic systems so that it did not contain wet strength additives. The paper was made up of approximately 65% eucalyptus and 35% northern softwood. Use of an organosolv pulp (e.g., see, U.S. Pat. No. 4,100,016 to Diebold, et al.) is also included in the Examples below.

Once the approximately optimum molarity of NaOH is established, the optimal ratio of co-solvents is established. While 75% was chosen by earlier investigators, they did not explore the potential of 70% or of 80%. In varying the ratio, it is important to avoid levels of ethanol that can result in precipitation of NaOH.

Figure 2:
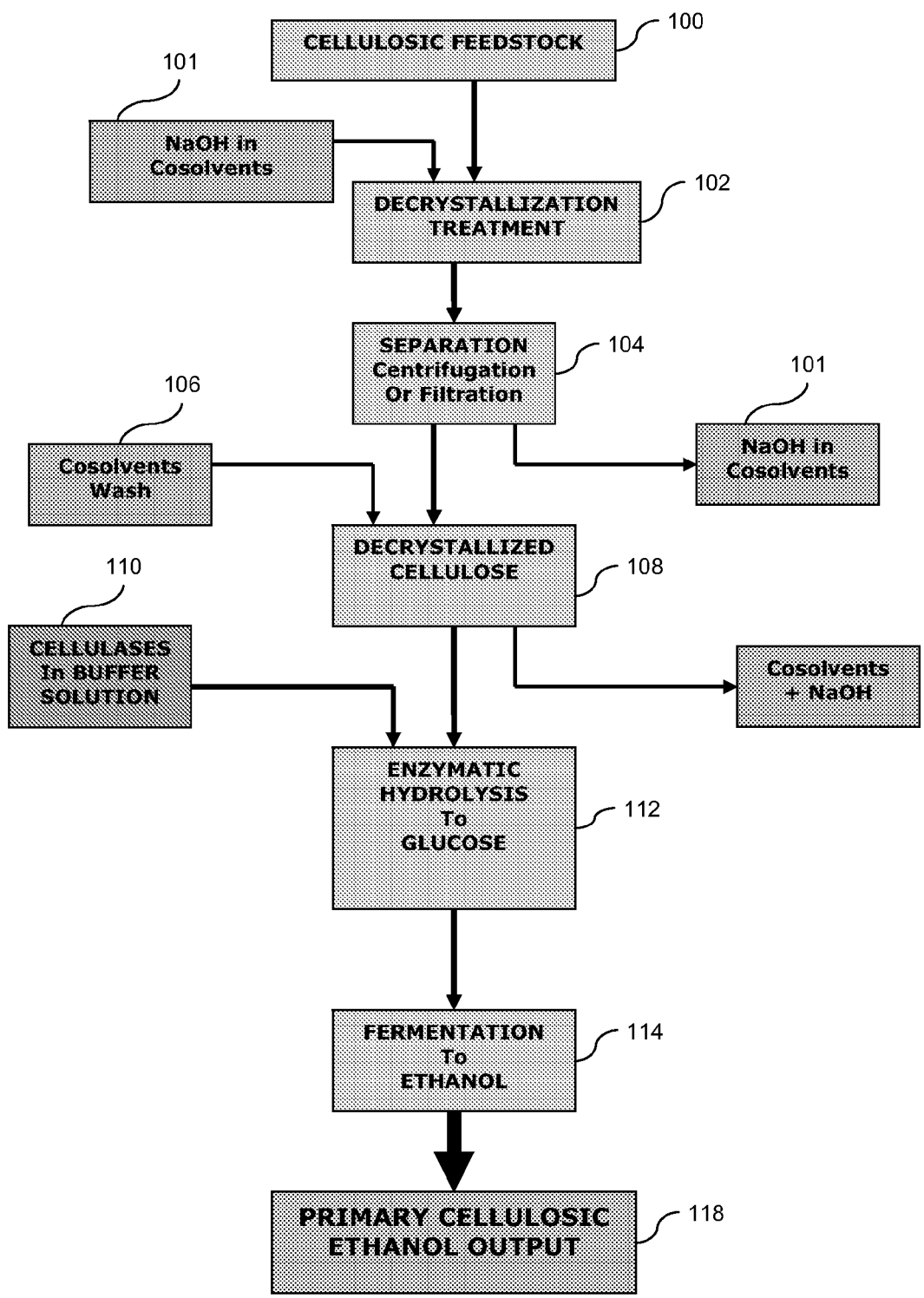
FIG. 2 is a flowchart illustrating a system in accordance with embodiments of the invention including the pretreatment of cellulosic feedstock to increase its accessibility to depolymerization.

Reference is now made to FIG. 2 that illustrates the general treatment process for embodiments in accordance with the invention as well as further steps in the processing of cellulosic feedstock to an alcohol, e.g., ethanol. The process begins at step 100 with a cellulosic source. In an illustrated embodiment, Avicel was used as a source of cellulose at step 100.

At step 102, the cellulosic material is subjected to a pretreatment step in accordance with embodiments of the invention, i.e., a treatment solution of alkali in a co-solvent system 101 of water and a second solvent, such as an alcohol, e.g., ethanol, or another water-miscible solvent, to decrystallize the cellulose. At step 104, the reaction mixture is separated to yield the decrystallized cellulose 108 and remove the treatment solution 101. At step 106, the treated cellulose is washed with a washing co-solvent solution or mixture 107 to remove the alkali. The washing co-solvent or mixture is suitably an alcohol/water mixture. At step 112, the treated cellulose in accordance with embodiments of the invention is hydrolyzed, for example, by treatment with cellulases 110, to form sugars. At step 114, the sugars, which include glucose and cello-oligodextrins, are suitably fermented, and a cellulosic alcohol 118 is recovered from the fermentation mix via distillation or other separatory method, e.g., membrane separation.

The effectiveness of the treatment solution is suitably measured by the onset of disruption of the Raman spectrum of cellulose, particularly in the low frequency region between 250 $cm^{-1}$ and 600 $cm^{-1}$ wherein the band at 378 $cm^{-1}$ is a very sensitive index of the degree of perturbation of the native lattice.

As to the washing mixture 107, if methanol was used as the co-solvent with water, it has been found that the same ratio of methanol to water as in the treatment co-solvent system is suitable for washing the NaOH out of the cellulose. For the ethanol/water system, a suitable ratio was also the same as in the treatment co-solvent.

It was noted earlier that the work with methanol was based on using the same ratio of co-solvents as in the pretreatment and was used as the starting point for ethanol/water co-solvent. The effect of varying the initial co-solvent for the first wash was determined. From a process perspective, it is especially suitable if the co-solvent ratio in the washing mixture is higher in ethanol than that used for the pretreatment as that would reduce the cost of post treatment of the washing solution. However, it is again noted that it is necessary to ensure that the ethanol content of the initial wash is not high enough to cause precipitation of NaOH.

After the first wash is completed, it is necessary to continue washing the cellulose substrate until a neutral pH is achieved. It was found in some cases that it was more effective to transition from the first wash to washes with co-solvents including higher levels of water, before eventually washing with water only.

Figure 3:
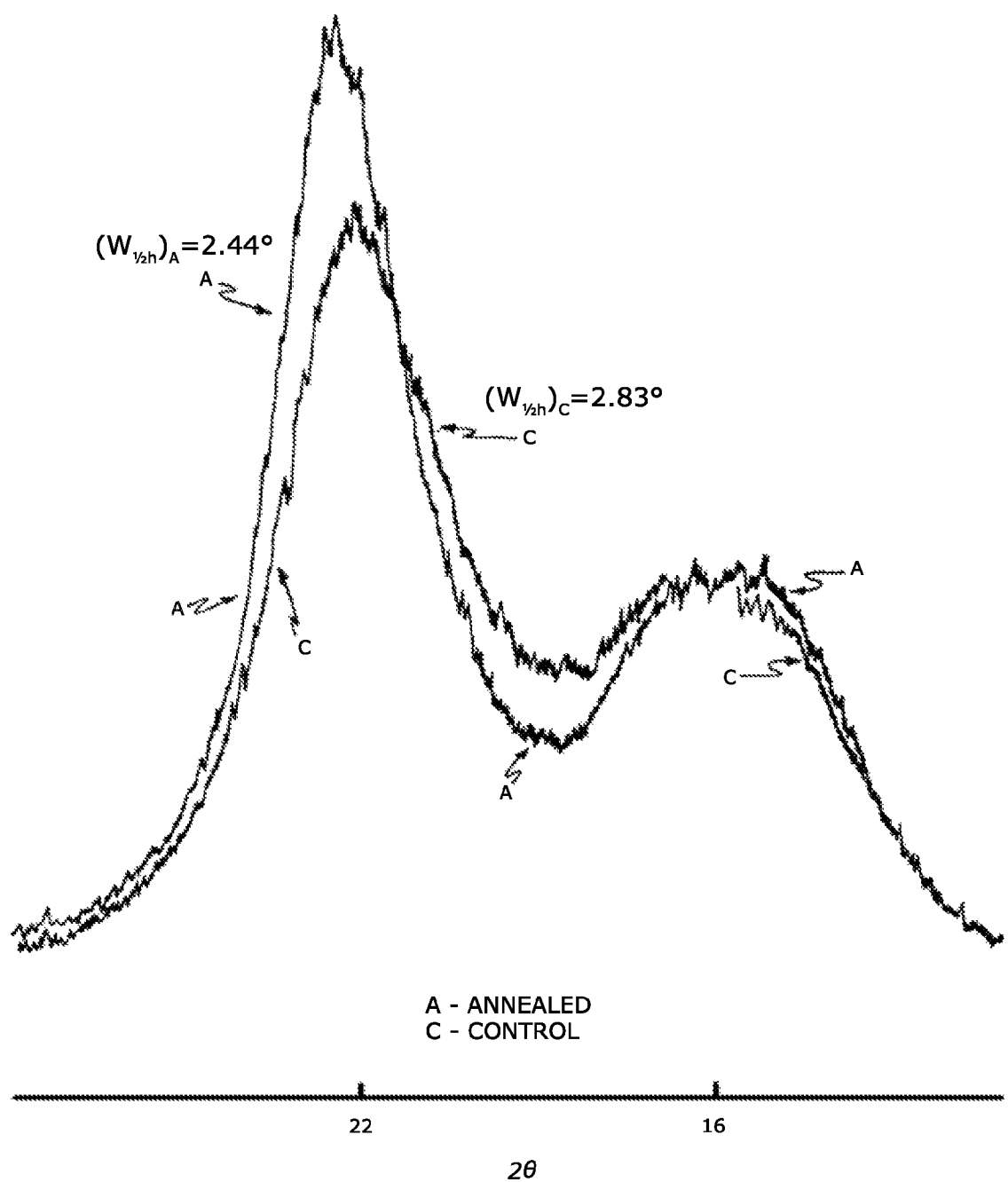
FIG. 3 shows comparative x-ray diffractograms of a cellulose isolated at 70° C. before and after it is annealed at 150° C.
Figure 4:
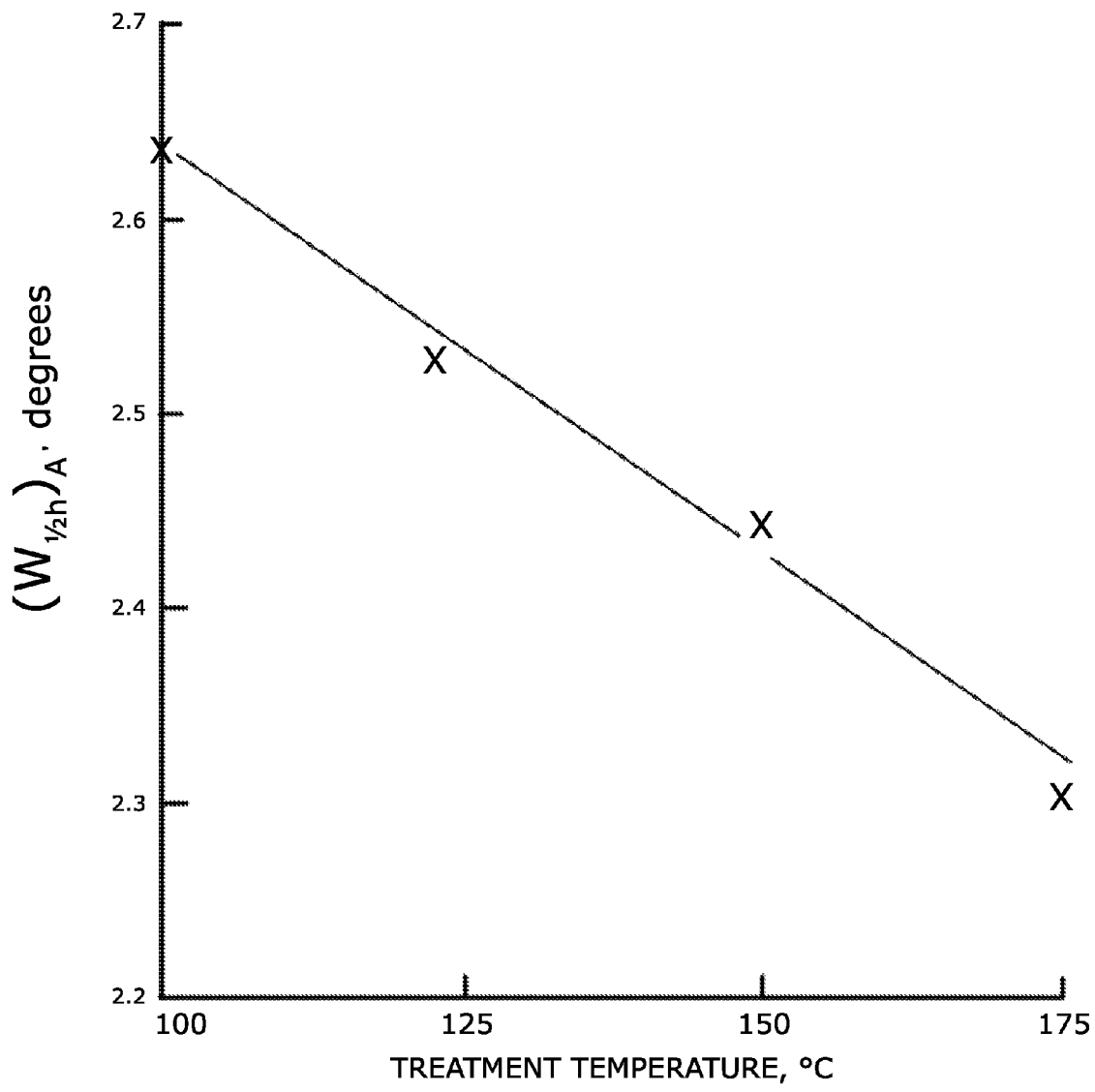
FIG. 4 is a graph of widths at half-height of cellulose samples annealed at different temperatures.

It has also been found that the degree to which the cellulose is tightly aggregated, and hence, its recalcitrance, is related to the highest temperature to which the cellulose is exposed during isolation (5). See, FIGS. 3 and 4 taken from the Atalla et al. reference (5). FIG. 3 shows the dramatic reduction in the width at half-height of the primary diffraction peak of native celluloses as a result of the annealing at 150° C. The width at half-height for the most prominent reflection in powder diffraction patterns of wood celluloses has always been regarded as one of the most sensitive indices of the degree of coherence of order within the cellulose in the wood cell walls. FIG. 4 shows how the width at half height declines as the temperature of treatment increases. Thus, in essence, the recalcitrance of a cellulosic sample is directly correlated with the temperature of isolation.

Once treated and washed, the degree to which the treated cellulose has become more accessible, i.e., decrystallized, can be assessed. Simple analytical methods, such as the weight loss upon enzymatic hydrolysis, can and were used as the measure of success in decrystallizing cellulose. Methods utilizing accessibility to deuterium oxide ($D_2O$) of the decrystallized cellulose can also be used. While these methods can rank the treatments, the readiness with which deuterium exchanges with hydrogen suggests that the use of $D_2O$ may result in overstating the degree of accessibility. It has been found that deuterated ethylene glycol ($OHCD_2CD_2OH$) appropriately assesses the degree of accessibility to enzymatic action.

In utilizing deuterated methods, the most common measures of accessibility have relied on observation of the access to cellulosic hydroxyl groups on the basis of perfusion of samples with $D_2O$ (4). While this is a useful measure, a more reliable measure is based on accessibility to molecules larger than the $D^+$ ion. Such molecules suitably include perdeutero methanol ($CD_3OH$), perdeutero ethylene glycol ($CD_2OHCD_2OH$), and perdeutero glycerol ($CD_2OHCDOHCD_2OH$), which can be added to the pretreated cellulosic samples in solution in $H_2O$, and allowed to reach equilibrium. The amount of deuterated molecules within the cellulosic samples is monitored through measurement of the Raman spectra of the samples in the region between 2300 and 2700 $cm^{-1}$ where there will be no interference from any other functional groups. The preparation of the perdeuterated samples of the alcohols or polyols can be accomplished by refluxing in $D_2O$ over Raney nickel.

Perdeuterated methanol is available commercially, and perdeuteration of glycol and glycerol can be carried out as noted above. The perdeuterated methanol is used in measurements based on using other celluloses that are common standards such as Avicel, which is derived from dissolving pulps, and Whatman CF-1 powder, which is derived from cotton linters. These standards are pre-swollen using known protocols.

As most enzymes are much larger in size than the molecules used to assess cellulose accessibility, an assay was developed for the transformations of the celluloses more closely related to the activity of enzymes. In such assay, the pretreated and washed cellulose are incubated with representative cellulases from *Aspergilus niger* and *Trichoderma reesi* to assess the effect of the transformations on susceptibility to enzyme action. As noted earlier, the increased availability of celluloses to the hydrolytic enzymes should increase the rate of conversion to sugars by at least one order of magnitude or more.

Reference is again made to FIG. 2 wherein it is noted that a portion of the alcohol, e.g., ethanol, produced, i.e., reference numeral 118, can be used in the decrystallization step 102 as the co-solvent. Thus, in accordance with embodiments of the invention, the entire cellulose conversion process may suitably have a feedback loop to supply co-solvent for the pretreatment process.

It is noted that a barrier to economic implementation of enzymatic hydrolysis of celluloses is the biphasic nature of the process when the celluloses are subjected to hydrolytic enzymes on a continuous basis in a batch process. The very long residence times required for the second phase result in the need for very large holding tanks to accommodate the time needed for the second phase to be complete. In another embodiment, it is envisioned that the long residence times of enzymatic hydrolysis reactions due to its biphasic nature can be reduced by use of the treatment process in accordance with embodiments of the invention. To overcome this barrier, the application of the enzymes can suitably be accomplished in multiple stages, with the cellulosic substrates subjected to the treatment in accordance with embodiments of the invention between stages.

Figure 5:
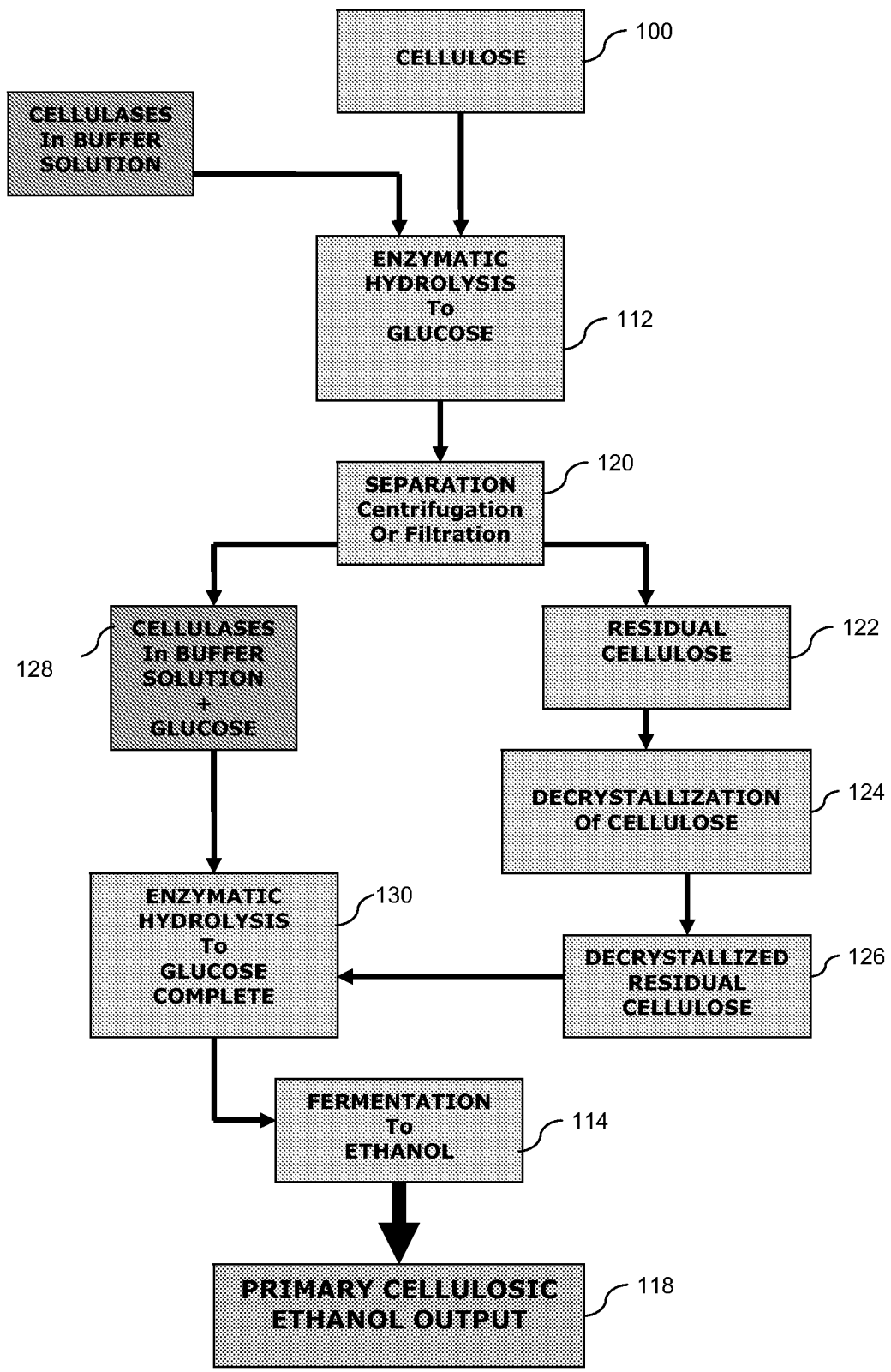
FIG. 5 is a flow chart describing an embodiment in accordance with principles of the invention, wherein the enzymes are applied without prior pretreatment followed by separation of the residual cellulose, pretreatment according principles of the invention, and then recombination with the supernatant from the separation after the first stage.

At least three such multistage processes are contemplated. As shown in FIG. 5, a first application of enzymatic hydrolysis is carried out in a first stage prior to a pretreatment as described herein in order to take advantage of the relatively rapid early phase in enzymatic hydrolysis. When the rate of hydrolysis has slowed down at the beginning of the second phase, the solid cellulosic residue is separated and pretreated as described herein, and then recombined with the supernatant liquid stream separated from the solids at the end of the first phase. Specifically, a cellulosic material 100 is subjected to enzymatic hydrolysis 112 with cellulose until the first phase of enzymatic hydrolysis begins to slow. At step 120, the reaction mixture is separated into residual cellulose 122 and the remainder 128 of cellulases and glucose. The residual cellulose 122 is subjected to the decrystallization 124 as illustrated in FIG. 2, to yield a decrystallized residual cellulose 126 which is subjected to enzymatic hydrolysis 130 again, utilizing remainder enzymatic solution 128. The sugar products are then fermented at step 114 to produce cellulosic ethanol 118.

Figure 6:
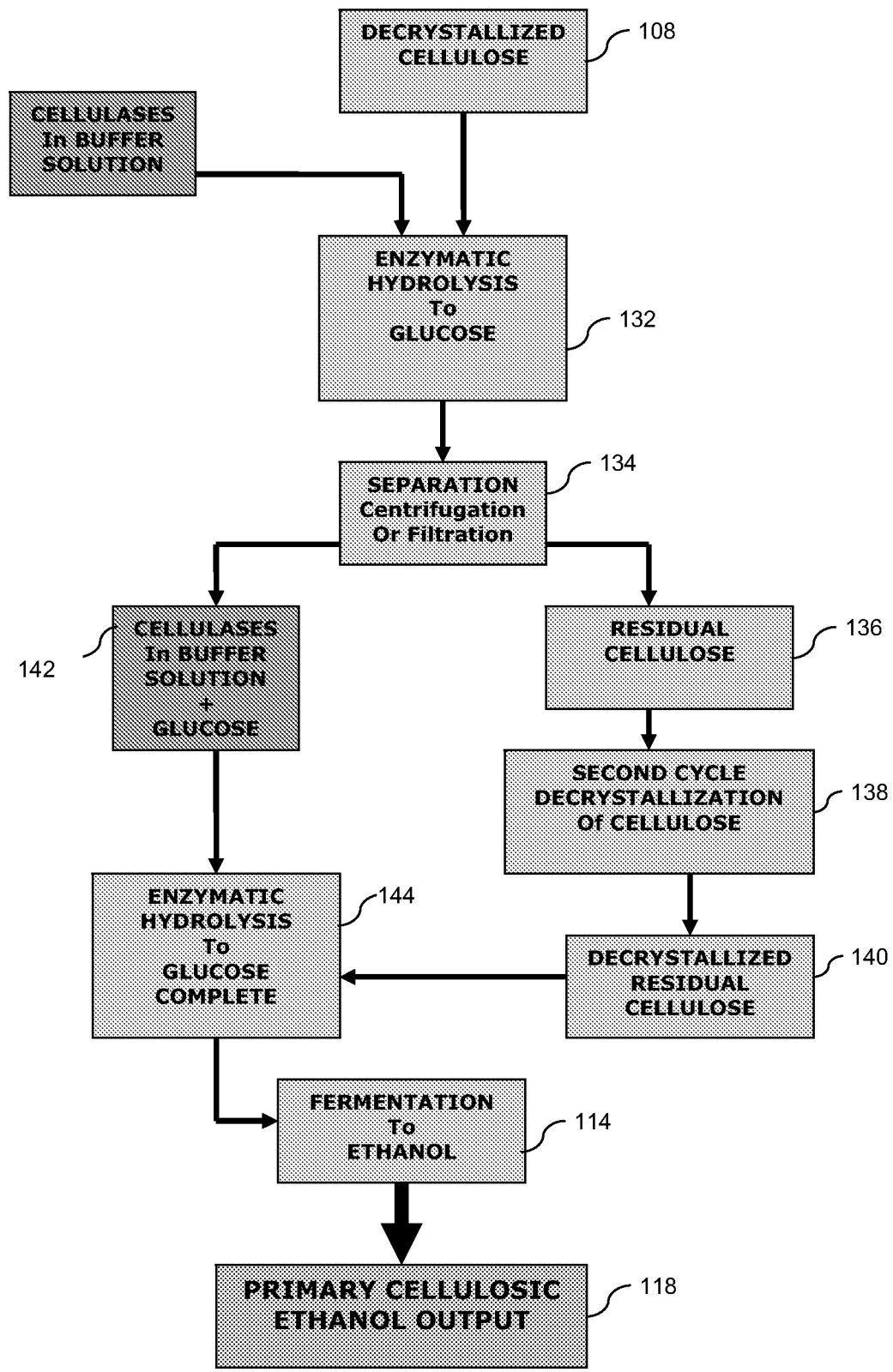
FIG. 6 is a flowchart illustrating an alternative embodiment for reducing enzymatic reaction times in accordance with principles of the invention, including treating the residual cellulose from a first stage pretreatment with second stages of decrystallization and enzymatic hydrolysis to glucose before fermentation to ethanol.

An embodiment of a second multistage process is shown in FIG. 6, and is based on repeating the decrystallization process as described herein between hydrolytic stages. At step 132, a decrystallized cellulose 108 as described herein is exposed to the enzymes for a period corresponding to the early phase of rapid hydrolysis. Next, at step 134, the residual cellulose 136 is separated from the enzyme-containing liquid medium 142 by filtration or centrifugation. The residual cellulose 136 is then subjected to a second cycle of decrystallization at step 138, as illustrated in FIG. 6, to yield a decrystallized residual cellulose 140, which, in turn, is exposed again to the enzyme-containing buffered water solution 142 for enzymatic hydrolysis to glucose at step 144 before fermentation to cellulosic ethanol 118 at step 114. It is anticipated that the hydrolysis again proceeds at a rapid rate so that the hydrolysis of the cellulose can be completed in a much shorter period than in the case of a single stage hydrolysis. Thus, one of the major cost factors in processes based on current designs, which need very long holding periods or residence times in the enzyme solution, is overcome and significantly reduced.

Figure 7:
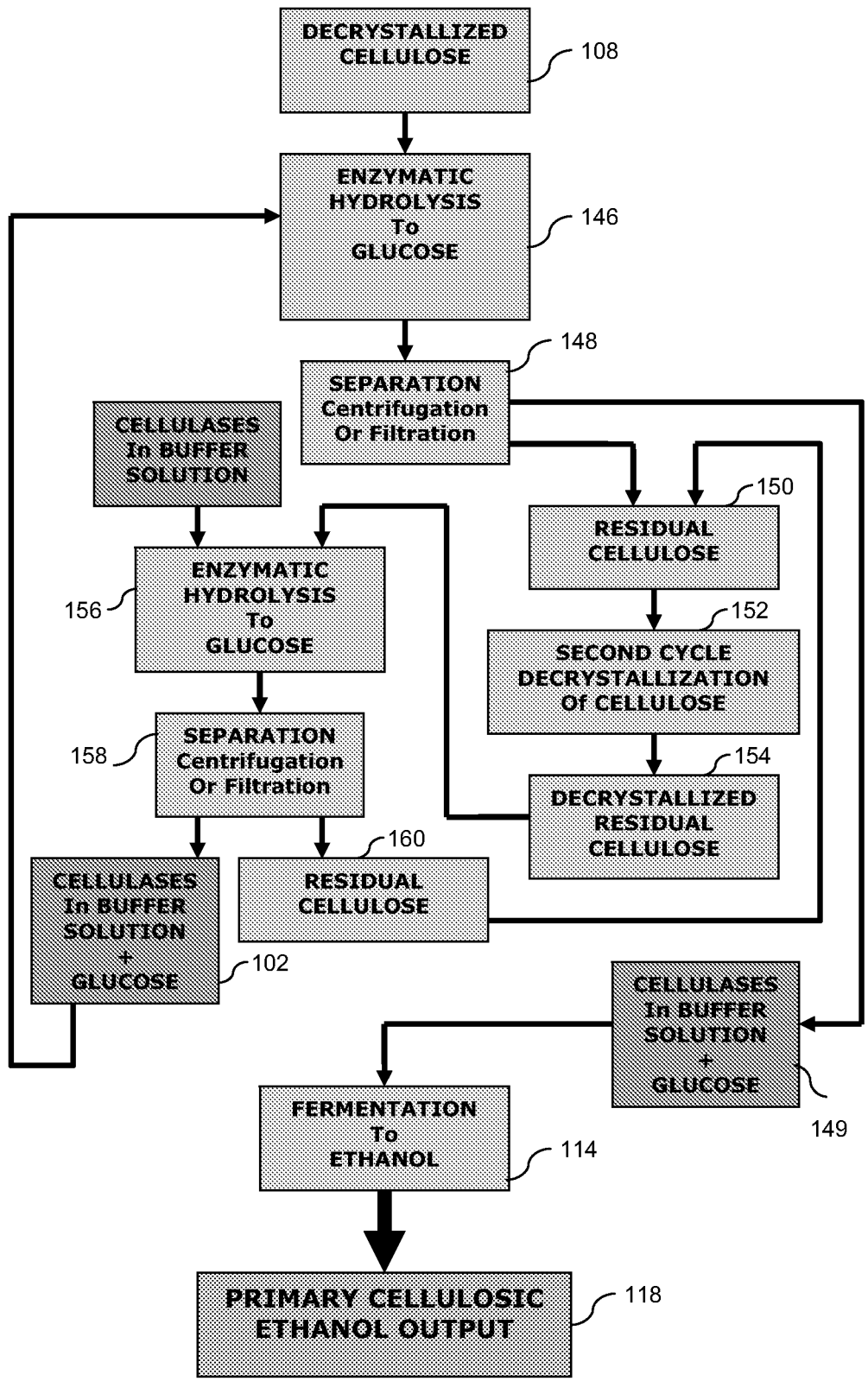
FIG. 7 is a flowchart illustrating yet another embodiment in accordance with principles of the invention for reducing enzymatic reaction times in accordance with principles of the invention utilizing a countercurrent system wherein the residual cellulose from the second stages of treatment is recirculated into the first stage of pretreatment.

An embodiment of a third multistage process is shown in FIG. 7, and includes a countercurrent mixing of the cellulose and the enzyme solutions. At step 146, a decrystallized cellulose 108 as described herein, is exposed to the enzymes. At step 148, the residual cellulose 150 is separated from the enzyme-containing liquid medium 149 by filtration or centrifugation. The residual cellulose 150 is subjected to a second cycle of decrystallization at step 152 to yield a decrystallized residual cellulose 154, which in turn is exposed again to the enzyme-containing buffered water solution at step 156. As shown in FIG. 7, fresh enzyme may be used at step 156 in the second stage of treatment, and after the second stage of treatment, the residual cellulose 160 is separated at step 158, and then introduced into a second cycle of decrystallization 152 to yield a decrystallized residual cellulose 154, and then reintroduced into the enzymatic solution 156. Furthermore, after filtration or complete dissolution at step 158 of the cellulose, the enzyme solution 102 is re-applied to decrystallized cellulose at step 146. The sugar products are then fermented at step 114 to produce cellulosic ethanol 118. Such an approach reduces the amount of enzyme needed for the conversion of the cellulose to glucose. The cost of the enzymes is another major economic barrier for processes based on current designs.

The specific embodiment in this third multistage process will depend on the nature of the cellulosic feedstock. If the cellulose was relatively pure, it is anticipated that the conversion may be complete before the enzyme-containing solution is added to the freshly decrystallized cellulose. However, if the feedstock contains other components of lignocellulosic matter, a filtration or centrifugation stage would be required prior to using the enzyme solution from the second stage to treat the feedstock in the first stage.

An embodiment of the invention is also contemplated as a kit, the kit including an alkali in an alcohol/water co-solvent, cellulase enzymes, one or more flocculants, and instructions for decrystallizing the cellulose to produce a decrystallized cellulose and instructions for hydrolyzing the decrystallized cellulose to produce a hydrolysis product.

It is further envisioned that a similar treatment may make the cellulose more accessible to solutions of homogeneous catalysts that may be used to transform the cellulosic feedstock into other forms. For example, the decrystallized cellulose as described herein could be more easily penetrated by the catalytic systems to reform it into hydrocarbons. Such process could make possible use of the vast amount of cellulosic resources as feedstocks for catalytic reformation to generate biofuels, such as diesel, fuel gases, such as hydrogen, and other high-value chemical types. Thus, in some embodiments, a method of producing cellulosic biofuels is provided. The method includes treating a cellulosic material with an alkali in an alcohol/water co-solvent system to yield a decrystallized cellulose; washing the decrystallized cellulose to remove the alkali; hydrolyzing the cellulose to glucose and cello-oligodextrins; and catalytically reforming the glucose and cello-oligodextrins into hydrocarbons.

As noted above, a barrier to much broader use of cellulose as a feedstock in the manufacture of fibers or films is the difficulty in solubilizing the cellulose in an environmentally acceptable system. The systems most often used outside of the United States are based on the century-old cellulose xanthate process, which is environmentally objectionable because the regeneration of the cellulose from solution results in the formation of hydrogen sulfide, and other toxic byproducts. The more recently developed methyl morpholine-N-oxide system relies on a complex and expensive solvent that is prone to explosion if conditions are not carefully controlled. On the other hand, the co-solvent system used herein is environmentally benign. It is envisioned that this system could alter dramatically the economics of rayon and cellophane manufacture as well as biofuels as described herein.

As noted above, embodiments of the invention also provide a novel nano-deaggregated cellulose which has a number of properties that differ significantly from those of other celluloses. Two key properties are of significant commercial interest at the present time. First, nano-deaggregated cellulose possesses a greater and more rapid accessibility at the nanoscale level to reagent molecules that are to be used for the modification of the celluloses. That is, there is greater accessibility to large reagent and enzymatic molecules intended to modify or react with the celluloses, e.g., greater accessibility to penetration of enzymes that may be used to hydrolyze the celluloses to produce glucose as a feedstock for fermentation into biofuels. As demonstrated in the Examples below, nano-deaggregated cellulose is more easily penetrated by large molecules and more easily hydrolyzed by cellulolytic enzymes. A second, equally important, property is a dramatic increase in the elasticity of nano-deaggregated cellulose modified to possess the novel internal state of molecular aggregation. These changes are important for developing better performance properties of cellulosic fiber networks formed during the manufacture of absorbent products or for application in filtration.

The following Examples, which should not be construed by way of limiting the scope of the invention, further explain embodiments of the invention. Moreover, all experimental processes may be further optimized for efficiency, and the process of scale up is expected to achieve greater enhancement of efficiency in the production of the novel nano-deaggregated cellulose and of conversion of this cellulose to sugars.

EXAMPLES

Experiments to demonstrate reduction of the recalcitrance of cellulose were carried out in two stages. The first included the process of treatment of the native cellulose. The second assessed the consequence of this treatment by exposing the treated cellulose samples to hydrolytic enzymes and measuring its weight loss in comparison to a control consisting of the untreated native cellulose from the same source.

The cellulose chosen as the substrate for the first Example was from a sample of Avicel PH1, which has been used as a standard in the inventor's laboratory since the 1970s and was supplied by the American Viscose Company (Marcus Hook, Pa.). It is a microcrystalline cellulose usually manufactured by acid hydrolysis of a high purity dissolving grade northern softwood pulp followed by mechanical disintegration of the pulp fibers and spray drying of the resulting dispersion of fiber fragments. This type of cellulose was chosen because Avicel has become a standard substrate in studies of enzymatic hydrolysis of cellulose and is representative of the most recalcitrant pulp-derived celluloses. In a second set of Examples, a kraft pulp derived from toilet paper was used. In yet another Example, an organosolv pulp was used.

The enzymes used in the assessments were a cellulase from the fungus Trichoderma reesi purchased from Worthington and a glucosidase derived from almonds available from Sigma Aldrich.

Example 1

Decrystallization and Preparation of Deaggregated Cellulose

A solution prepared for treatment of the Avicel was a 1.5 N solution of sodium hydroxide (NaOH) in a mixture of ethanol ($CH_3CH_2OH$) and water that was 75% ethanol by volume. To prepare the treatment solution, ethanol and water were mixed, and then 6 g of NaOH was dissolved per 100 mL of the solvent mixture.

The treatment procedure was as follows: 1 g of Avicel was placed in a 300 mL beaker. To this, 50 mL of the treatment solution were added. The Avicel was allowed to sit in the treatment solution for 15 minutes. Thereafter, the solution was decanted and replaced with 100 mL of the solvent mixture (75% ethanol, 25% water). This solution was allowed to sit for a few minutes to allow diffusion of the NaOH out of the cellulose.

The solvent was then decanted and the process repeated two times whereupon the pH was approximately 8. After decanting the solvent the last time, a solution of 0.05 M ammonium acetate buffer at a pH of 5 was added; the pH was 5.4 after the rinse in buffer. The buffer solution was decanted, and 30 mL of buffer added again; the pH was then determined to be 5.0.

The dispersion of cellulose in 30 mL of buffer was transferred to a 50 mL polypropylene centrifuge tube and buffer added to the 40 mL level. Hydrolytic enzymes were added to the tube. These enzymes were 0.2 g cellulase (108 µ/mg) and 0.1 g β-glucosidase (6 µ/mg).

A control sample of 1 g of untreated Avicel was also placed in a 50 mL polypropylene centrifuge tube, and 40 mL of buffer added to it, followed by addition of the same amounts of enzymes as the test sample.

The two centrifuge tubes were then tightly closed with their covers, and inserted in a Vortemp 1550 shaking incubator. The contents of the tubes were incubated at 45° C. and agitated at a speed of 900 rpm. It was found necessary to agitate at 900 rpm to keep the cellulose microcrystalline particles adequately dispersed.

For a first experiment, the incubation was for 41 hrs, and for a second, the incubation was for 13 hrs.

After the incubation, the two dispersions were each divided into 8 portions in 15 mL centrifuge tubes. The tubes were inserted in a centrifuge and spun for 2 minutes at 3800 rpm. The buffer-enzyme liquid was decanted from each tube and replaced with 95% ethanol, re-dispersed and spun again; this was done twice for each of the samples. The last ethanol decanted was replaced with acetone followed by dispersion in the acetone.

The acetone dispersions were then, in turn, poured into tared crucibles with sintered glass bottom filters; the crucible filters were mounted on a vacuum flask with full vacuum applied during the filtration. The crucibles were then transferred to a vacuum oven with full vacuum applied, heated to 105° C., and held at that temperature under vacuum overnight.

The samples were then weighed on an analytical balance, and the weight loss taken as a measure of the conversion of cellulose to glucose and soluble oligomers.

It should be noted that the 1.5 M (or 1.5 N) solution of NaOH in the solvent mixture was selected because the Avicel microcrystalline cellulose was derived from a dissolving pulp. Had microcrystalline cellulose made from cotton linters been used, it would have been necessary to use a 2 M (or 2 N) solution of NaOH in the solvent. Conversely, if the cellulose had been isolated from a herbaceous plant at a temperature much closer to ambient temperature, a 1 M (or 1 N) solution may have been adequate. This variability in the normality required for the pretreatment of cellulose reflects the great diversity in the level of aggregation of celluloses from different sources and with different histories into semicrystalline domains.

Results:

As noted above, the initial weights of the test and control samples were 1 g each. The weights after exposure to the enzyme mixture at 45° C. are given below in Table 1.

TABLE 1

| Incubation time | Control | Pretreated | Δ |
| --- | --- | --- | --- |
| 13 hrs | 0.535 g | 0.408 g | 0.127 g |
| 41 hrs | 0.251 g | 0.189 g | 0.062 g | where Δ represents the difference in weight loss between the control and pretreated samples. Thus, in both instances the loss in weight of the sample treated as described herein was significantly greater than that of the control sample.

The results demonstrated that the loss in weight for both samples during the first 13 hr exposure was significantly higher than the loss during the further exposure for an additional 28 hrs. This is typical of the biphasic nature of enzyme action on celluloses where the rate of conversion to glucose or soluble oligomers proceeds rapidly at first but then levels off to a much slower rate. The results of these experiments demonstrate that the decrystallization treatment described herein increases the disorder in cellulose substrates at the nano-level to yield a new form of cellulose, nano-deaggregated cellulose, which is more susceptible to enzymatic hydrolysis by cellulases.

Example 2

A Two Stacie Process

A solution prepared for treatment of the Avicel was a 1.5 N solution of sodium hydroxide (NaOH) in a mixture of ethanol ($CH_3CH_2OH$) and water that was 75% ethanol by volume. To prepare the treatment solution, one mixes the ethanol and water, and then dissolves 6 g of NaOH per 100 mL of the solvent mixture.

The treatment procedure was as follows: 2 samples of 1 g each of Avicel were placed in 50 mL centrifuge tubes, one experimental sample, and one control. To each, 45 mL of 0.05 N ammonium acetate buffer with a pH of 5.01 was added. Both tubes received 0.15 g of cellulase, which was assayed at 136 μ/mg DW, with no supplemental β-glucosidase.

Both samples were placed in a Vortemp 1550 shaking incubator. They were incubated at 50° C. and agitated at a speed of 900 rpm. Initial incubation was for 5.5 hours.

After the initial incubation period, the experimental sample was removed from the incubator and chilled in an ice bath to halt the enzyme action. The experimental sample was then placed in a centrifuge and spun at 4500 rpm to extract the supernatant. The supernatant was decanted and set aside for later return to the sample tube.

The sample tube then had 50 mL of the NaOH treatment solution added, and was shaken for 5 minutes, after which it was placed back in the centrifuge to extract the treatment solution.

Thereafter, the solution was decanted and replaced with 50 mL of the solvent mixture (75% ethanol, 25% water). It was shaken for 5 minutes to allow diffusion of the NaOH out of the cellulose. It was then centrifuged at 4500 rpm.

The solvent was then decanted and the process repeated two times. After the last decanting of solvent, a solution of 0.05 M ammonium acetate buffer at a pH of 5.01 was added; the pH was 8.4 after dispersing the sample in buffer. The buffer solution was centrifuged and decanted and 40 mL of buffer added again; the pH was then determined to be 5.15. This cycle was repeated one more time, after which the pH of the sample in buffer was 5.04. The buffer was then removed.

The supernatant enzyme solution extracted previously was returned to the sample tube, and incubation was resumed at 50° C. and 900 rpm. The second phase of incubation lasted 2.5 hours.

After the incubation, both experimental and control sample tubes were inserted in a centrifuge and spun for 2 minutes at 4500 rpm. The buffer-enzyme liquid was decanted from each tube, and the remaining solids poured onto tared fiberglass paper for drying in a microwave oven with a built-in analytical balance, with the weight loss taken as a measure of the conversion of cellulose to glucose and soluble oligomers.

Results:

As noted above, the initial weights of the test and control sample were 1 g each. The weight after exposure to the enzyme mixture at 50° C. is given below in Table 2.

TABLE 2

| Incubation time | Control | Pretreated | Δ |
|---|---|---|---|
| 8 hrs | 0.529 g | 0.269 g | 0.26 g | where Δ represents the difference in weight loss between the control and pretreated samples. Thus, in both instances the loss in weight of the sample treated as described herein was significantly greater than that of the control sample.

Example 3

A Two Stacie Treatment Using a Kraft Pulp Paper

A solution prepared for treatment of toilet paper (Cottonelle™ brand) was a 1.5 N solution of sodium hydroxide (NaOH) in a mixture of ethanol ($CH_3CH_2OH$) and water that was 75% ethanol by volume. Preparation of the treatment solution was the same as described in previous examples The treatment procedure was as follows: 2 samples (one control and one experimental sample) of toilet paper were weighed and then cut into small pieces and placed in 50 mL centrifuge tubes. The tubes were filled with water and put in a Vortemp 1550 shaking incubator at room temperature at 900 rpm and left to disperse overnight.

Each tube was filled to the 50 mL mark with 0.05 N ammonium acetate buffer with a pH of 5.01. Both tubes received 0.125 g of cellulase, which was assayed at 136 μ/mg DW, with no supplemental β-glucosidase. Both samples were placed in the Vortemp incubator. They were incubated at 50° C. and agitated at a speed of 900 rpm. Initial incubation was for 4.25 hours.

After the initial incubation period, both samples were removed from the incubator and chilled in an ice bath to halt the enzyme action. The experimental sample was then placed in a centrifuge and spun at 4500 rpm to extract the supernatant. The supernatant was decanted and set aside for later return to the sample tube.

The sample tube then had 50 mL of the NaOH treatment solution added, and was shaken for 2 minutes, after which it was placed back in the centrifuge to extract the treatment solution.

Thereafter, the solution was decanted and replaced with 50 mL of the solvent mixture (75% ethanol, 25% water). It was shaken for 2 minutes to allow diffusion of the NaOH out of the cellulose.

The solvent was then decanted and the process repeated two times. After decanting the solvent the last time, a solution of 0.05 M ammonium acetate buffer at a pH of 5.01 was added; the pH was 6.4 after dispersing the sample in buffer. The buffer solution was centrifuged and decanted and 40 mL of buffer added again; the pH was then determined to be 5.23. The supernatant enzyme solution extracted previously was returned to the sample tube, and incubation was resumed at 50° C. and 900 rpm. The second phase of incubation lasted approximately 9.5 hours.

After the incubation, both experimental and control sample tubes were inserted in a centrifuge and spun for 2 minutes at 4500 rpm. The buffer-enzyme liquid was decanted from each tube, and the remaining solids poured onto tared fiberglass paper for drying in a microwave oven with a built-in analytical balance, with the weight loss taken as a measure of the conversion of cellulose to glucose and soluble oligomers.

Results:

The initial weights of the test and control samples, along with the weights after exposure to the enzyme mixture at 50° C. are given below in Table 3.

TABLE 3

|  | Initial wt | Final wt | % conversion |
|---|---|---|---|
| Control | 1.021 g | 0.314 g | 69.25% |
| Pretreated | 1.026 g | 0.226 g | 77.97% |

The difference in the percentage of sample weight remaining demonstrates that conversion of the sample treated as described herein was greater than that of the control sample.

Example 4

A Single Stacie Treatment Using a Kraft Pulp Paper

A solution prepared for treatment of toilet paper (Cottonelle™ brand) was a 1.5 N solution of sodium hydroxide (NaOH) in a mixture of ethanol ($CH_3CH_2OH$) and water that was 75% ethanol by volume. Preparation of the treatment solution was the same as described in previous examples.

The treatment procedure was as follows: 2 samples (one control and one experimental sample) of toilet paper were weighed and then cut into small pieces and placed in 50 mL centrifuge tubes. The tubes were filled with water and put in a Vortemp 1550 shaking incubator at room temperature at 900 rpm and left to disperse overnight.

The experimental sample was put in a centrifuge for 2 minutes at 4500 rpm and the extracted water decanted. The tube was refilled with 200 proof ethanol, and shaken for 5 minutes at 900 rpm, after which the tube was centrifuged again, the ethanol decanted, and then the tube was refilled with a mix of 75% ethanol and 25% water, shaken for 5 minutes, centrifuged and decanted again.

The sample tube then had 50 mL of the NaOH treatment solution added, and was shaken for 5 minutes, after which it was placed back in the centrifuge to extract the treatment solution.

Thereafter, the solution was decanted and replaced with 50 mL of the solvent mixture (75% ethanol, 25% water). It was shaken for 5 minutes to allow diffusion of the NaOH out of the cellulose.

The solvent was then decanted and the process repeated two times. After decanting the solvent the last time, a solution of 0.05 M ammonium acetate buffer at a pH of 5.01 was added; the pH was 12.63 after dispersing the sample in buffer. The buffer solution was centrifuged and decanted and 40 mL of buffer added again; the pH was then determined to be 9.37. This cycle was repeated 4 more times, with the pH determined at 6.02, 5.29, 5.14, and then 5.05 in the last cycle.

The control tube was filled to the 50 mL mark with the same ammonium acetate buffer solution. Both tubes received 0.125 g of cellulase, which was assayed at 136 μ/mg DW, with no supplemental β-glucosidase. Both samples were placed in a Vortemp 1550 shaking incubator. They were incubated at 50° C. and agitated at a speed of 900 rpm for a total incubation of 16 hours and 25 minutes.

After the incubation, both experimental and control sample tubes were inserted in a centrifuge and spun for 2 minutes at 4500 rpm. The buffer-enzyme liquid was decanted from each tube, and the remaining solids poured onto tared fiberglass paper for drying in a microwave oven with a built-in analytical balance, with the weight loss taken as a measure of the conversion of cellulose to glucose and soluble oligomers.

Results:

The initial weights of the test and control samples, along with the weights after exposure to the enzyme mixture for 16 hours and 25 minutes at 50° C. are given below in Table 4.

TABLE 4

|  | Initial wt | Final wt | % conversion |
|---|---|---|---|
| Control | 1.020 g | 0.367 g | 64.02% |
| Pretreated | 1.017 g | 0.225 g | 77.88% |

The difference in the percentage of sample weight remaining demonstrates that conversion of the sample treated as described herein was greater that of the control sample.

In general, the enzymatic hydrolysis conversion to soluble saccharides appears to be at least 70%.

Example 5

A Two Stacie Treatment Using an Organosolv Pulp

An organosolv pulp (e.g., U.S. Pat. No. 4,100,016) was initially treated with sodium chlorite to delignify it, after which it was allowed to air dry. The sodium chlorite treatment is a well-established, mild bleaching technique. Two samples (one control and one experimental sample) were weighed out from the resulting delignified, dried pulp.

A solution prepared for treatment of the delignified organosolv pulp was a 1.5 N solution of sodium hydroxide (NaOH) in a mixture of ethanol ($CH_3CH_2OH$) and water that was 75% ethanol by volume. Preparation of the treatment solution was the same as described in previous examples.

The treatment procedure was as follows: 2 samples (one control and one experimental sample) of pulp were weighed and then placed in 50 mL centrifuge tubes. The tubes were filled with water and put in a Vortemp 1550 shaking incubator at room temperature at 900 rpm and left to disperse for two days. After dispersion, both tubes were put in a centrifuge and spun at 4500 rpm for about 3 minutes, after which the water was decanted.

Each tube was then filled to the 50 mL mark with 0.05 N ammonium acetate buffer with a pH of 5.01. Both tubes received 0.2 g of cellulase, which was assayed at 136 μ/mg DW, with no supplemental β-glucosidase. Both samples were placed in the Vortemp incubator. They were incubated at 50° C. and agitated at a speed of 900 rpm. Initial incubation was for 5.5 hours.

After the initial incubation period, both samples were removed from the incubator. The experimental sample was then placed in a centrifuge and spun for 7 minutes at 4700 rpm to extract the supernatant. The supernatant was decanted and set aside for later return to the sample tube.

The sample tube then had 50 mL of the NaOH treatment solution added, and was shaken for 2 minutes, after which it was placed back in the centrifuge to extract the treatment solution.

Thereafter, the solution was decanted and replaced with 50 mL of the solvent mixture (75% ethanol, 25% water). It was shaken for 2 minutes to allow diffusion of the NaOH out of the cellulose.

The solvent was then decanted and the process repeated two times. After decanting the solvent the last time, a solution of 0.05 M ammonium acetate buffer at a pH of 5.01 was added; the pH was 7.32 after dispersing the sample in buffer. The buffer solution was centrifuged and decanted and 40 mL of buffer added again; the pH was then determined to be 5.18. The supernatant enzyme solution extracted previously was returned to the sample tube, and incubation was resumed at 50° C. and 900 rpm. The second phase of incubation lasted approximately 3.5 hours.

After the incubation, both experimental and control sample tubes were inserted in a centrifuge and spun for 2 minutes at 4500 rpm. The buffer-enzyme liquid was decanted from each tube, and the remaining solids poured onto tared fiberglass paper for drying in a microwave oven with a built-in analytical balance, with the weight loss taken as a measure of the conversion of cellulose to glucose and soluble oligomers.

Results:

The initial weights of the test and control samples, along with the weights after exposure to the enzyme mixture at 50° C. are given below in Table 5.

TABLE 5

|  | Initial wt | Final wt | % conversion |
| --- | --- | --- | --- |
| Control | 1.003 g | 0.539 g | 46.26% |
| Pretreated | 1.005 g | 0.409 g | 59.3% |

The difference in the percentage of sample weight remaining demonstrates that conversion of the sample treated as described herein was greater than that of the control sample.

In summary, the deaggregated cellulose in accordance with embodiments of the invention has a greater enzymatic hydrolysis conversion to soluble saccharides than known celluloses, e.g., cellulose I, at the same concentration of enzyme.

Example 6

Characterization of Nano-Deaggregated Cellulose

Experiments were carried out to characterize nano-deaggregated cellulose in accordance with embodiments of the invention. In these experiments, x-ray diffractograms, Raman spectra, NMR spectra and grain/cell staining were obtained according to entirely conventional protocols.

X-ray Diffractometry Studies

As noted above and as further carried here, x-ray diffractograms studies were carried out to compare the structure of known celluloses with that of the novel nano-deaggregated cellulose in accordance with embodiments of the invention.

Known Celluloses and Amorphous Cellulose

Figure 8:
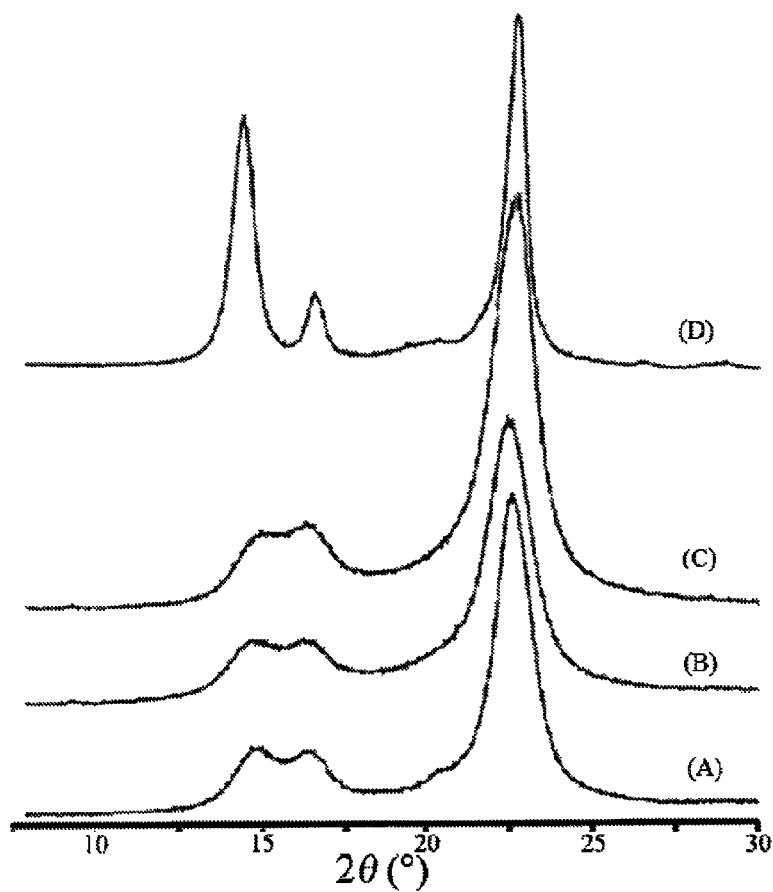
FIG. 8 shows x-ray diffractograms of known native celluloses.
Figure 9:
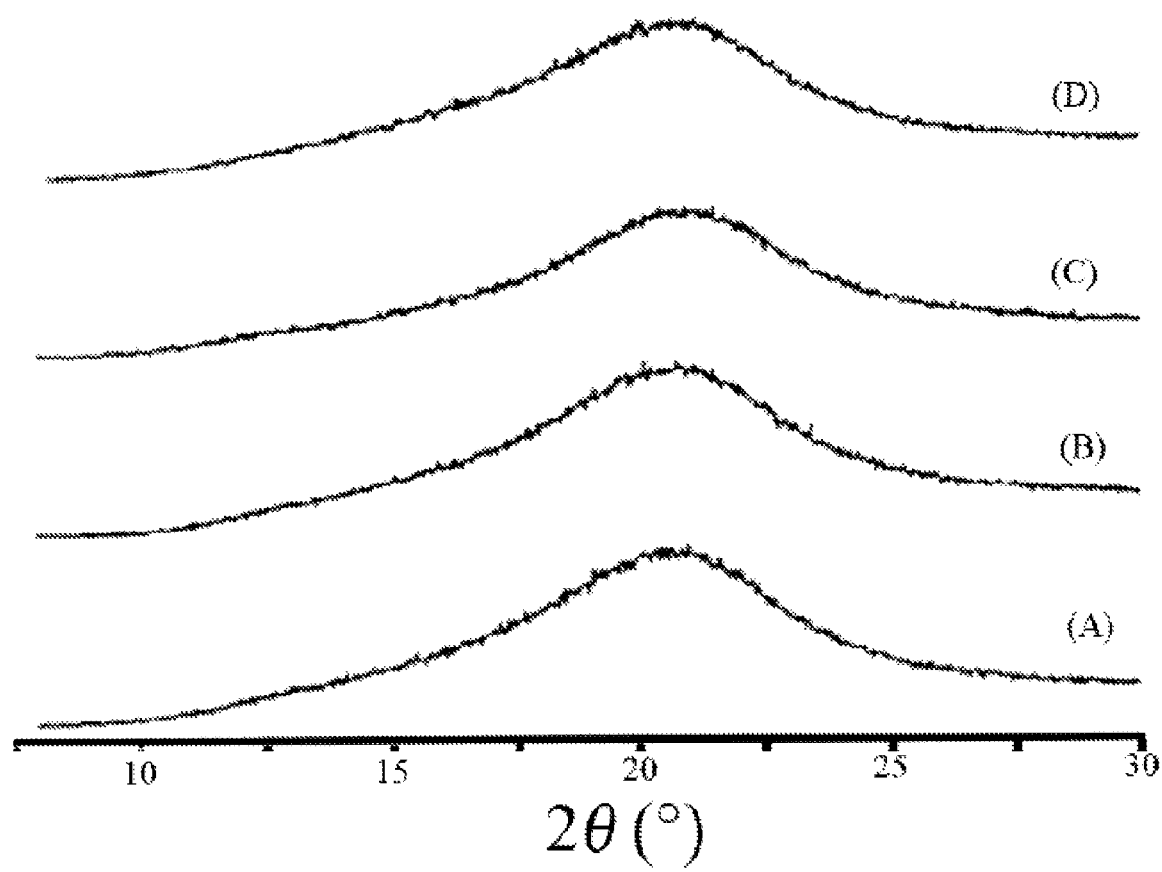
FIG. 9 shows x-ray diffractograms of randomly ordered, i.e., amorphous, celluloses.

Reference is first made to FIGS. 8 and 9 that show prior art x-ray diffractograms of four different native celluloses (FIG. 8) and amorphous cellulose (FIG. 9) prepared from the same four celluloses. (Isogai and Atalla, *Journal of Polymer Science: Polymer Chemistry*, 29 (1991) 113)

As to FIG. 8, the Whatman CF1 powder is made from cotton linters. Diffractograms A, B, and C are typical of highly ordered higher plant celluloses. The algal cellulose diffractogram D is representative of a class of algae that produce highly ordered cellulose microfibrils that are much larger in lateral dimensions than higher plant celluloses.

It should be noted here that the higher values of 2Θ represent narrower spacings between the diffracting entities. Thus, the peaks in the range of 2Θ values between 20° and 22° are representative of the typical spacings between adjacent anhydroglucose rings in an ordered cellulose. The width at half-height is often regarded as a measure of the degree of disorder in the aggregated celluloses.

All of the diffractograms of FIG. 9 are representative of highly disordered, almost randomly associated molecular chains of cellulose. In these diffractograms, there are no distinctive peaks in these diffractograms, although it is that the maxima are in the range of values of 2Θ between 20° to 22°

Kraft Pulp

Reference is again made to FIG. 1 which is an x-ray diffractogram of a bleached kraft pulp before and after the treatment process for disordering the original pulp cellulose into nano-deaggregated cellulose. It is to be noted that the diffractogram of the original pulp is typical for a commercial kraft pulp. The diffraction peak associated with the 020 planes occurs at approximately 22.8° 2Θ while the broader peak associated with the combined 110 and 1-10 peaks occurs between 14° and 16° 2Θ. In contrast, the diffraction peaks associated with nano-deaggregated cellulose occur at approximately 20° and 12° 2Θ. Two features of the diffractogram of nano-deaggregated cellulose are noteworthy. First, there is no sharp separation of the diffraction peaks at 20° and 12° 2Θ, but they are superimposed on a rather broad diffraction ranging from 10° to 24° 2Θ. The appearance of the two peaks, even though they are broad indicates that some residual order remains and that the molecular chains of cellulose remain parallel to each other. The decline in the values of 2Θ reflects an opening of the spacing between the chains. It was concluded that the spacing between the chains has been opened up, thus allowing the easy penetration of larger molecules within the partially ordered celluloses. Yet the retention of the parallel organization of the chains is key to maintenance of the microscale and macroscale morphology of the native celluloses.

FIGS. 10-16, discussed below, show x-ray diffractograms of celluloses derived from various sources. It is noted that the most significant and consistent change in x-ray patters of celluloses treated in accordance with principles of the invention is the broadening of the main 020 peak.

Avicel

Further x-ray diffractograms of untreated Avicel, treated Avicel and mercerized Avicel were obtained. As noted above, Avicel is a microcrystalline cellulose usually prepared from high purity dissolving pulps. Treated Avicel samples were prepared in accordance with the embodiments of the present invention, i.e., the Avicel was treated with a 1.5 N solution of NaOH in the co-solvent made of 75% ethanol and 25% water. It was then washed with the co-solvent three times then washed with water for three more times.

Figure 10:
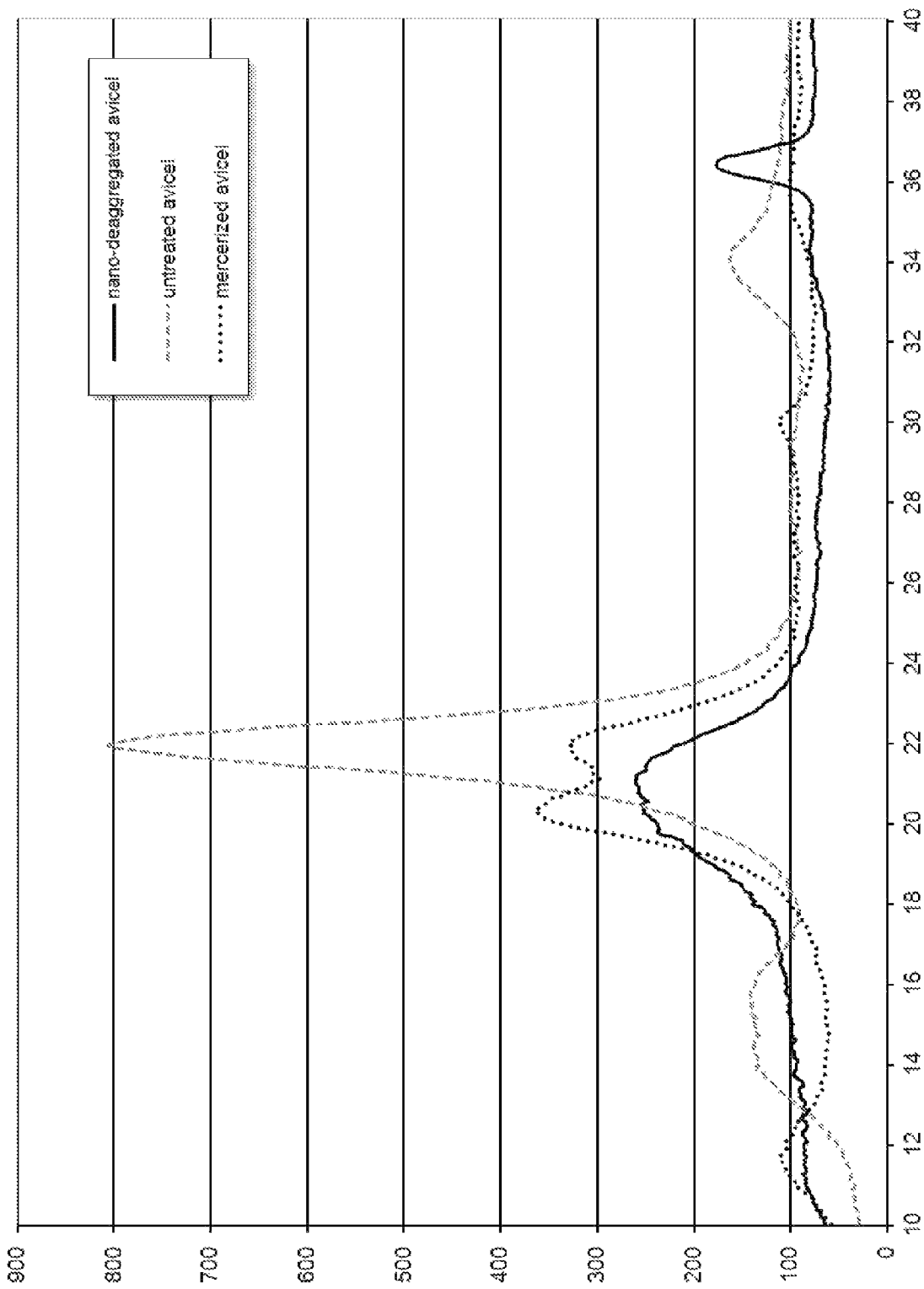
FIG. 10-16 show x-ray diffractograms of pulps before and after the pretreatment process in accordance with embodiments of the invention.

As seen in FIG. 10, the diffractogram of the untreated Avicel is very similar to the diffractograms B and C from FIG. 8, which are for cotton and ramie, both relatively pure higher plant celluloses. The diffractogram of the mercerized Avicel is typical of that of cellulose II, which is the form of cellulose produced by mercerization. The treated Avicel has a single broad peak that is shifted to lower values of 2Θ, which is indicative of somewhat greater spacing between the molecular chains as is characteristic of celluloses treated in accordance with embodiments of the invention.

The following x-ray diffractograms were also obtained for other cellulose source materials.

Corn Bran

Corn bran samples were prepared prior to treatment with the process of embodiments of the present invention as follows: The sample of biomass was subjected to extraction by methanol by reflux in a soxhelet extracting system for 3 to 4 hours. This was followed by similar extraction using 2 parts chloroform to 1 part methanol for 6 to 8 hours. This was followed by washing in 100% methanol, then a co-solvent of 50% methanol and 50% distilled water, and finally with 100% distilled water. The sample was then boiled in 0.25 N sodium hydroxide (NaOH) in water under reflux conditions for 2 hours under nitrogen. It was then rinsed in distilled water, and boiled for 3 more hours under nitrogen. It was rinsed again with water and bleached for 24 hours in a solution of 6 g sodium chlorite in 640 ml of water with 2 ml of glacial acetic acid added. It was then treated with the chelating agent diethylene triamine pentaacetic acid (DTPA) for 30 minutes, and the process repeated two more times. Finally, the sample was freeze dried. The prepared sample was then treated in accordance with embodiments of the present invention as described for Avicel samples above in FIG. 10.

Figure 11:
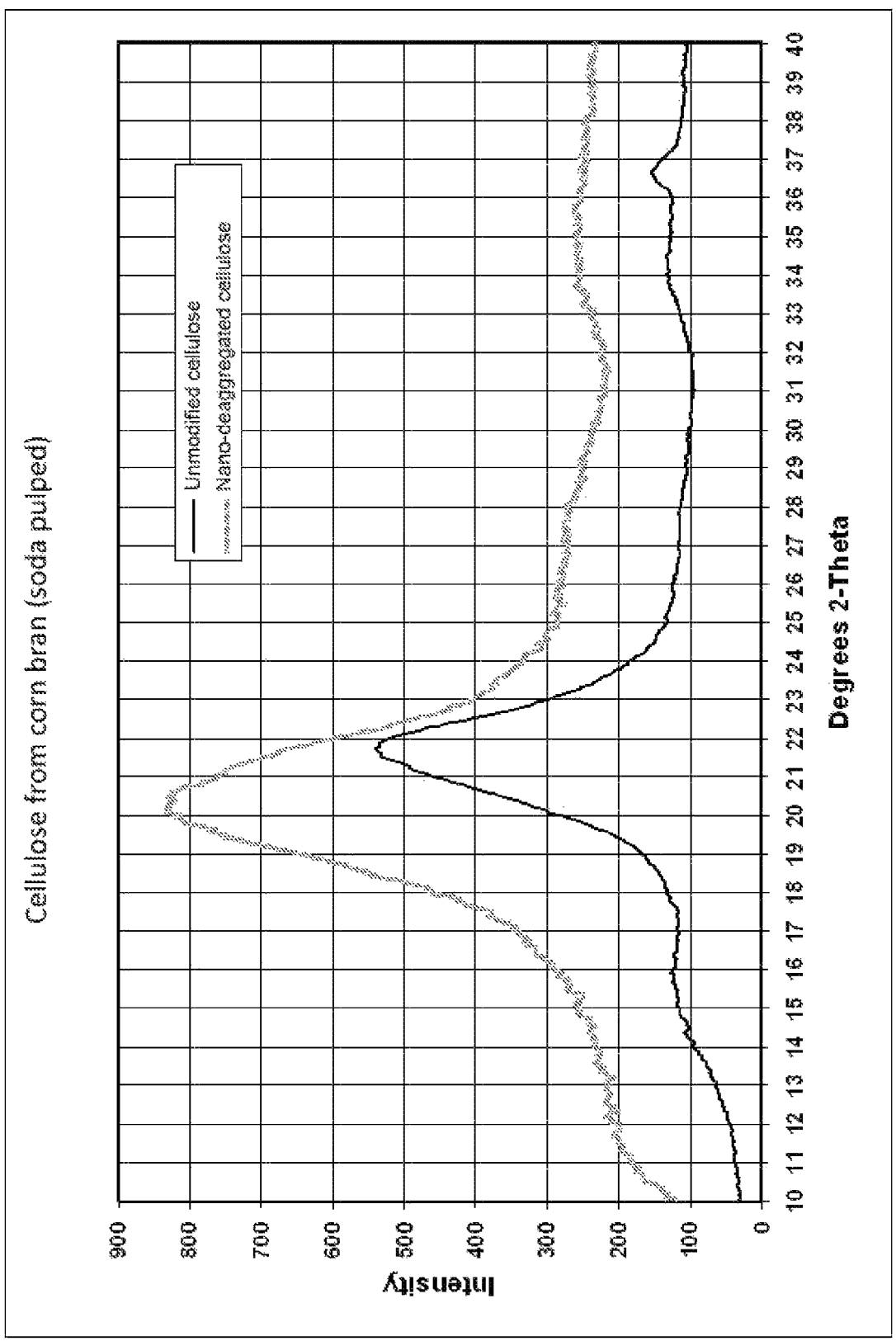

As seen in FIG. 11, diffractograms of treated and untreated cellulose from corn bran show that the spacings are dramatically increased as indicated by the shifting of the peak of the diffractogram to a lower value of 2Θ; they are also broadened, reflecting greater disorder. This pattern appears to be typical of celluloses that in their native state occur together with other cell walls polysaccharides. These other polysaccharides have been removed in the course of purification of the celluloses.

Fiber Sorghum

Fiber sorghum the samples were prepared prior to treatment with the process in accordance with embodiments of the invention as follows: The sample of biomass was subjected to extraction by methanol by reflux in a soxhelet extracting system for 3 to 4 hours. This was followed by similar extraction using 2 parts chloroform to 1 part methanol for 6 to 8 hours. This was followed by washing in 100% methanol, then a co-solvent of 50% methanol and 50% distilled water, and finally with 100% distilled water. The sample was then boiled in 0.25 N sodium hydroxide (NaOH) in water under reflux conditions for 2 hours under nitrogen. It was then rinsed in distilled water and boiled for 3 more hours under nitrogen. It was rinsed again with water, and bleached for 24 hours in a solution of 6 g sodium chlorite in 640 ml of water with 2 ml of glacial acetic acid added. It was then treated with the chelating agent diethylene triamine pentaacetic acid (DTPA) for 30 minutes, and the process repeated two more times. Finally the sample was freeze dried. The prepared samples were then treated as described for Avicel above in FIG. 10 in accordance with embodiments of the invention.

Figure 12:
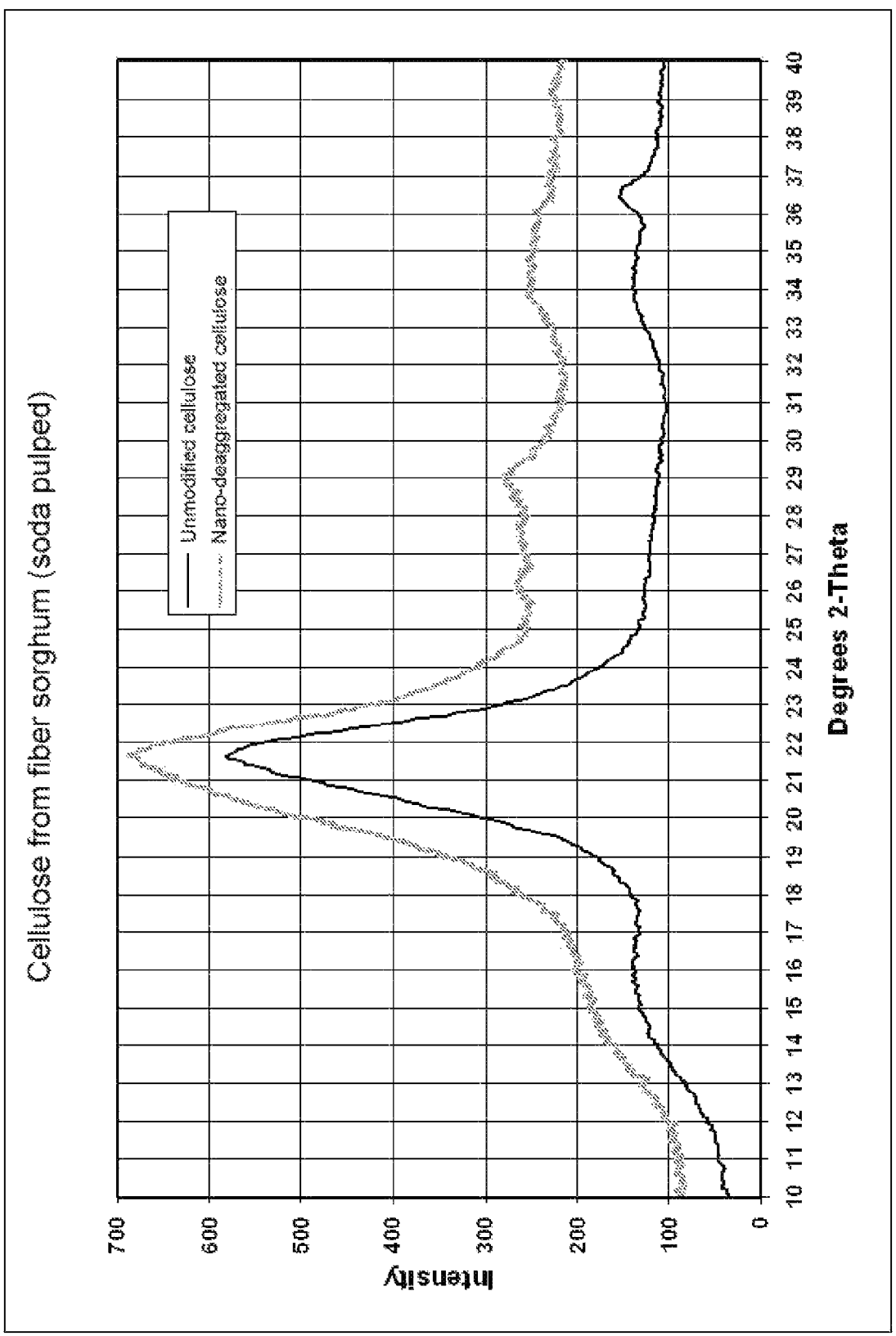

FIG. 12 shows diffractograms of cellulose from fiber sorghum that was untreated and that was treated in accordance with embodiments of the invention. The spacings are significantly broader although one does not see a shift of the peak of the diffractogram to a lower value of 2Θ. Though the broadening is typical of celluloses that in their native state occur together with other cell walls polysaccharides, it appears that differences in fiber morphology at the next level up can influence the response to the process in accordance with embodiments of the invention. Here again other polysaccharides have been removed in the course of purification of the celluloses.

Hybrid Poplar

Samples of hybrid poplar chips were prepared prior to treatment in accordance with embodiments of the invention as follows: The sample of biomass was subjected to extraction by methanol by reflux in a soxhelet extracting system for 3 to 4 hours. This was followed by similar extraction using 2 parts chloroform to 1 part methanol for 6 to 8 hours. This was followed by washing in 100% methanol, then a co-solvent of 50% methanol and 50% distilled water, and finally with 100% distilled water. The sample was then boiled in 0.25 N sodium hydroxide (NaOH) in water under reflux conditions for 2 hours under nitrogen. It was then rinsed in distilled water and boiled for 3 more hours under nitrogen. It was rinsed again with water and bleached for 24 hours in a solution of 6 g sodium chlorite in 640 ml of water with 2 ml of glacial acetic acid added. It was then treated with the chelating agent diethylene triamine pentaacetic acid (DTPA) for 30 minutes, and the process repeated two more times. Finally, the sample was freeze dried. The prepared samples were then treated as described for Avicel above in accordance with embodiments of the invention.

Figure 13:
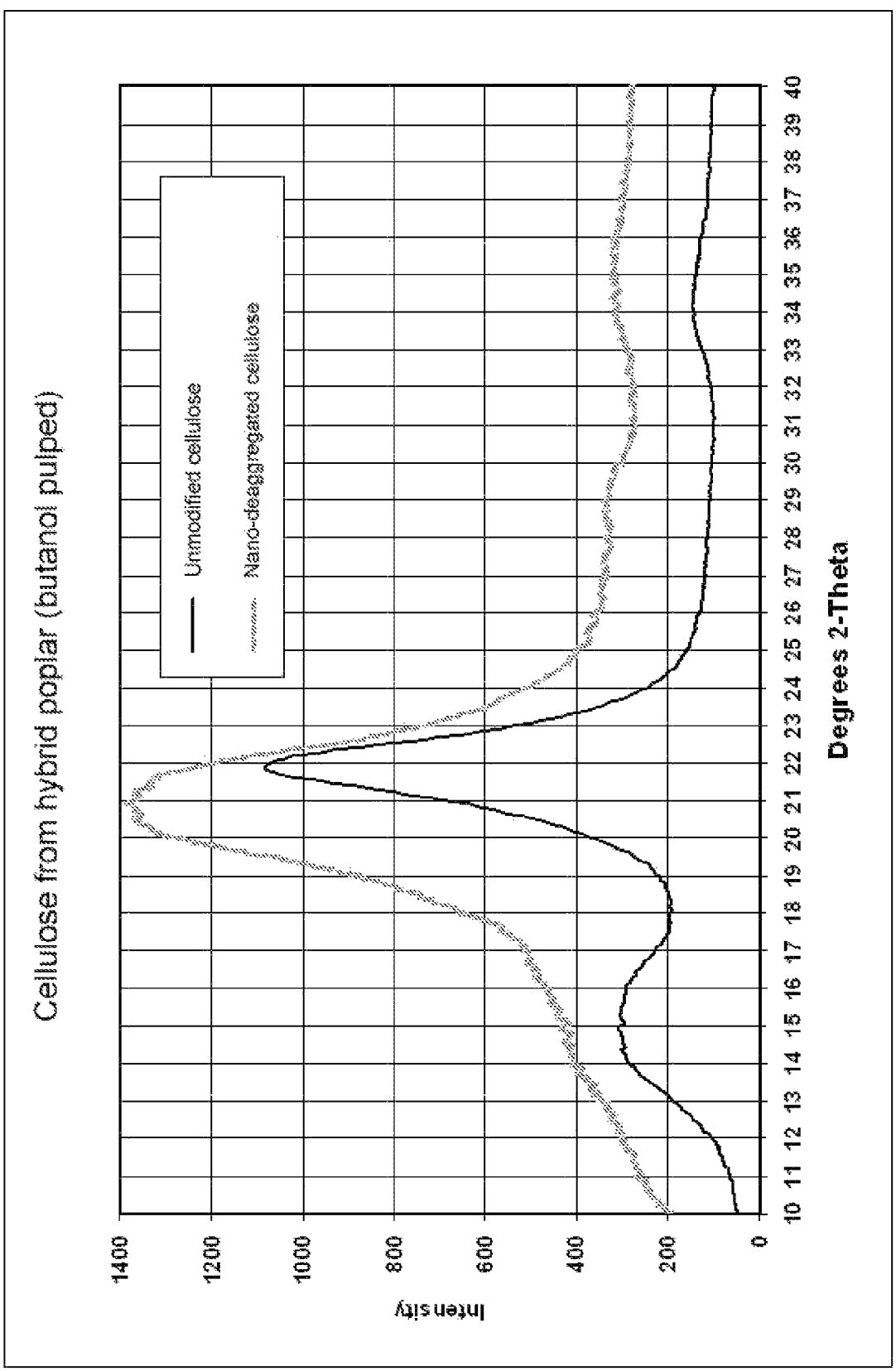
Figure 14:
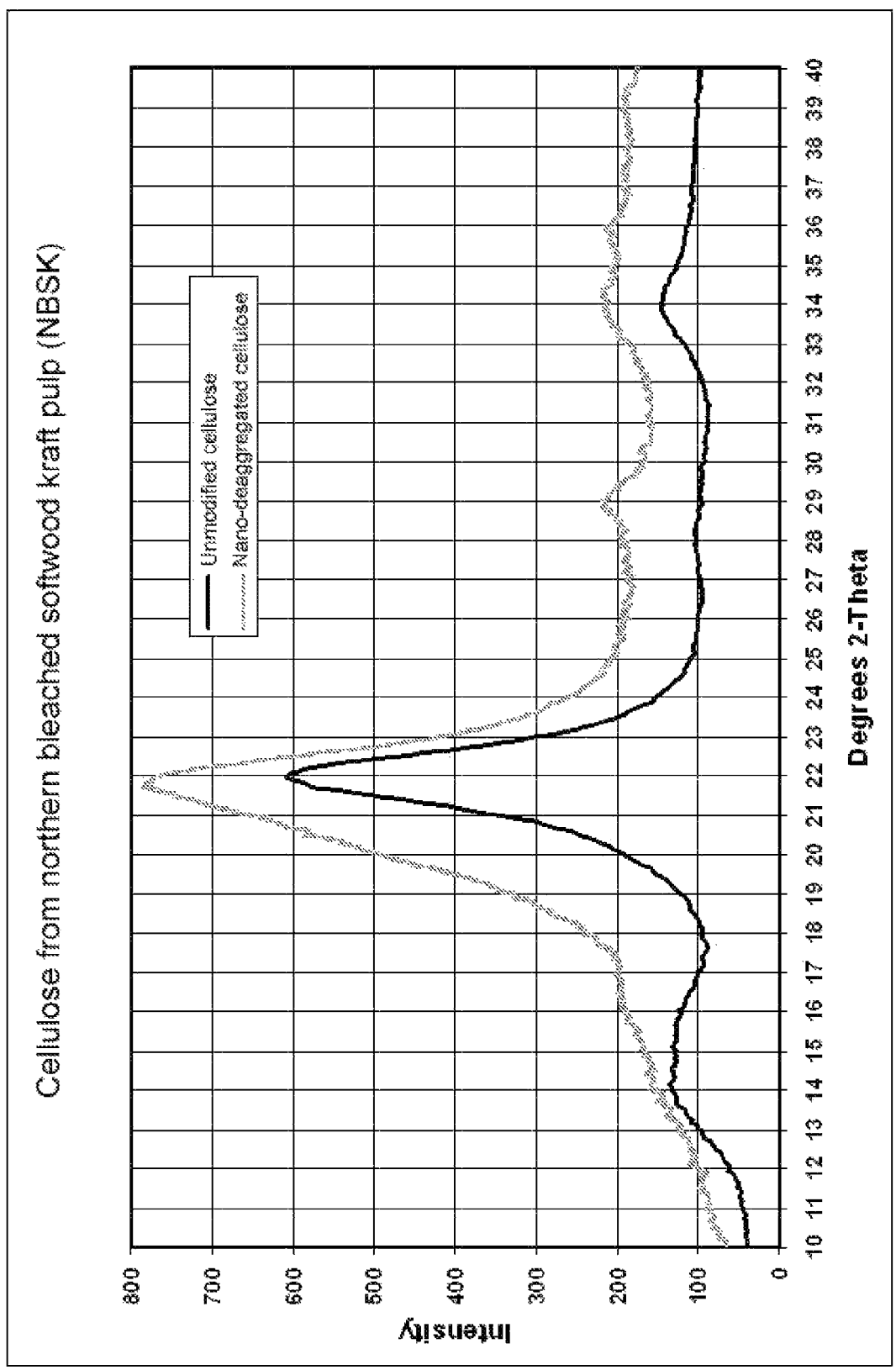

FIG. 13 shows diffractograms of cellulose from hybrid poplar chips that have been pulped. Here the pattern is similar to that for corn bran as one sees that the spacings are increased as indicated by the shifting of the peak of the diffractogram to a lower value of 2Θ. This pattern appears to be typical of celluloses that in their native state occur together with other cell walls polysaccharides. These other polysaccharides have been removed in the course of purification of the celluloses. Here again though as in the case of the fiber sorghum, higher levels of organization in the morphology seem to have an effect.

Northern Bleached Softwood

Samples of northern bleached softwood were prepared prior to treatment with the process in accordance with embodiments of the invention as follows: The sample of biomass was subjected to extraction by methanol by reflux in a soxhelet extracting system for 3 to 4 hours. This was followed by similar extraction using 2 parts chloroform to 1 part methanol for 6 to 8 hours. This was followed by washing in 100% methanol, then a co-solvent of 50% methanol and 50% distilled water, and finally with 100% distilled water. The sample was then boiled in 0.25 N sodium hydroxide (NaOH) in water under reflux conditions for 2 hours under nitrogen. It was then rinsed in distilled water, and boiled for 3 more hours under nitrogen. It was rinsed again with water and bleached for 24 hours in a solution of 6 g sodium chlorite in 640 ml of water with 2 ml of glacial acetic acid added. It was then treated with the chelating agent diethylene triamine pentaacetic acid (DTPA) for 30 minutes, and the process repeated two more times. Finally, the sample was freeze dried. The prepared samples were then treated as described for Avicel above in accordance with embodiments of the invention.

FIG. 13 shows diffractograms of cellulose from an untreated and treated northern bleached softwood. These diffractograms are not unlike those from fiber sorghum. Here again the spacings are significantly broader although here there is indeed a very small shift of the peak to a lower value of 2Θ. Though the broadening is typical of celluloses that in their native state occur together with other cell walls polysaccharides, here again it appears that differences in fiber morphology at the next level up do make a difference. Here also other polysaccharides have been removed in the course of purification of the celluloses.

Nekoosa Hardwood Chins

Nekoosa hardwood chip samples were prepared prior to treatment with the process in accordance with embodiments of the invention as follows: The sample of biomass was subjected to extraction by methanol by reflux in a soxhelet extracting system for 3 to 4 hours. This was followed by similar extraction using 2 parts chloroform to 1 part methanol for 6 to 8 hours. This was followed by washing in 100% methanol, then a co-solvent of 50% methanol and 50% distilled water, and finally with 100% distilled water. The sample was then boiled in 0.25 N sodium hydroxide (NaOH) in water under reflux conditions for 2 hours under nitrogen. It was then rinsed in distilled water, and boiled for 3 more hours under nitrogen. It was rinsed again with water and bleached for 24 hours in a solution of 6 g sodium chlorite in 640 ml of water with 2 ml of glacial acetic acid added. It was then treated with the chelating agent diethylene triamine pentaacetic acid (DTPA) for 30 minutes, and the process repeated two more times. Finally, the sample was freeze dried. The prepared samples were then treated as described for Avicel above in accordance with embodiments of the invention.

Figure 15:
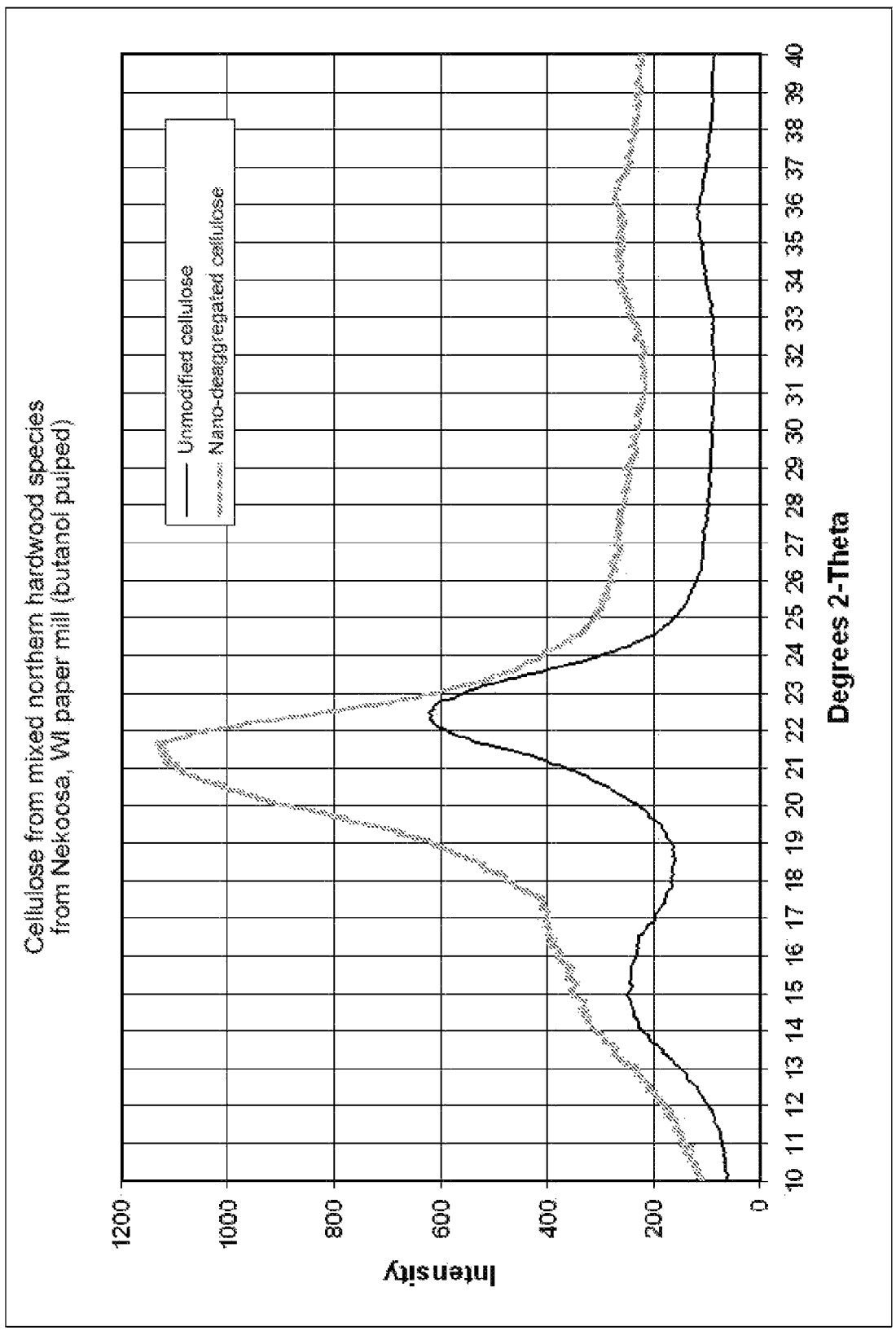

FIG. 15 shows diffractograms of cellulose hardwood chips from the Nekoosa mill that have been pulped. The diffractograms for treated and untreated samples are very similar to that of the hybrid poplar chips, i.e., the spacings are increased as indicated by the shifting of the peak of the diffractogram to a lower value of 2Θ. As noted above, this pattern appears to be typical of celluloses that in their native state occur together with other cell walls polysaccharides. These other polysaccharides have been removed in the course of purification of the celluloses. Here again, as in the case of the hybrid poplar, higher levels of organization in the morphology seem to have an effect.

Corn Stover

Corn stover samples were prepared prior to treatment with the process in accordance with embodiments of the invention as follows: The sample of biomass was subjected to extraction by methanol by reflux in a soxhelet extracting system for 3 to 4 hours. This was followed by similar extraction using 2 parts chloroform to 1 part methanol for 6 to 8 hours. This was followed by washing in 100% methanol, then a co-solvent of 50% methanol and 50% distilled water, and finally with 100% distilled water. The sample was then boiled in 0.25 N sodium hydroxide (NaOH) in water under reflux conditions for 2 hours under nitrogen. It was then rinsed in distilled water, and boiled for 3 more hours under nitrogen. It was rinsed again with water and bleached for 24 hours in a solution of 6 g sodium chlorite in 640 ml of water with 2 ml of glacial acetic acid added. It was then treated with the chelating agent diethylene triamine pentaacetic acid (DTPA) for 30 minutes, and the process repeated two more times. Finally, the sample was freeze dried. The prepared samples were then treated as described for Avicel above in accordance with embodiments of the invention.

Figure 16:
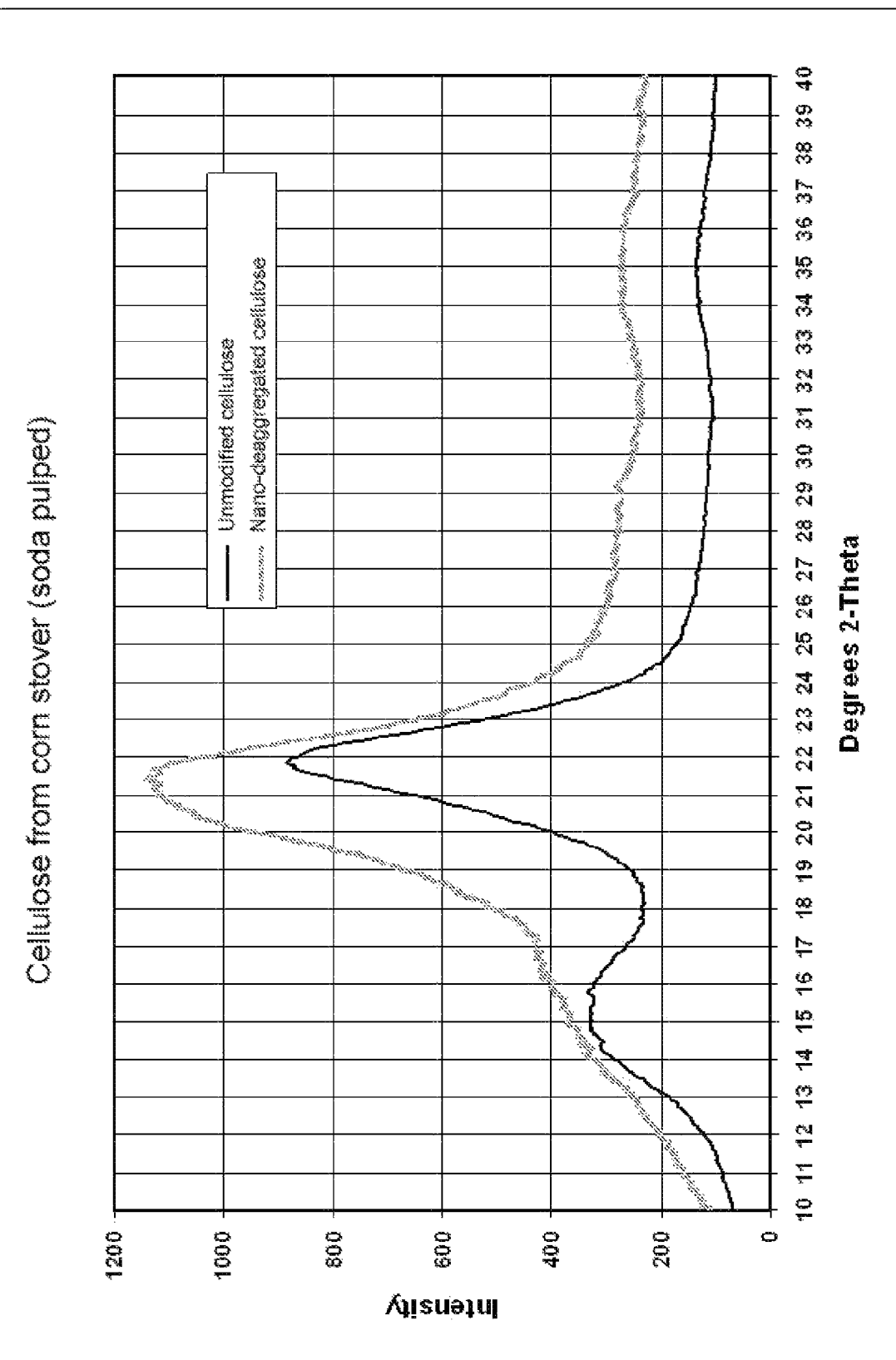

FIG. 16 shows diffractograms of cellulose from corn stover. These diffractograms are more like those of corn bran and the hardwoods than those of the fiber sorghum. The spacings are significantly broader although one sees only a relatively small shift of the peak of the diffractogram to a lower value of 2Θ. Though the broadening is typical of celluloses that, in their native state, occur together with other cell walls polysaccharides, the differences in fiber morphology at the next level are the most likely cause of the difference. Here again other polysaccharides have been removed in the course of purification of the celluloses.

These diffractograms show that the nano-deaggregated cellulose in accordance with embodiments of the invention is quite different from amorphous cellulose, and that the spacings between molecular chains is increased and has a broader distribution than in the original celluloses.

Raman Spectra Studies

Figure 17:
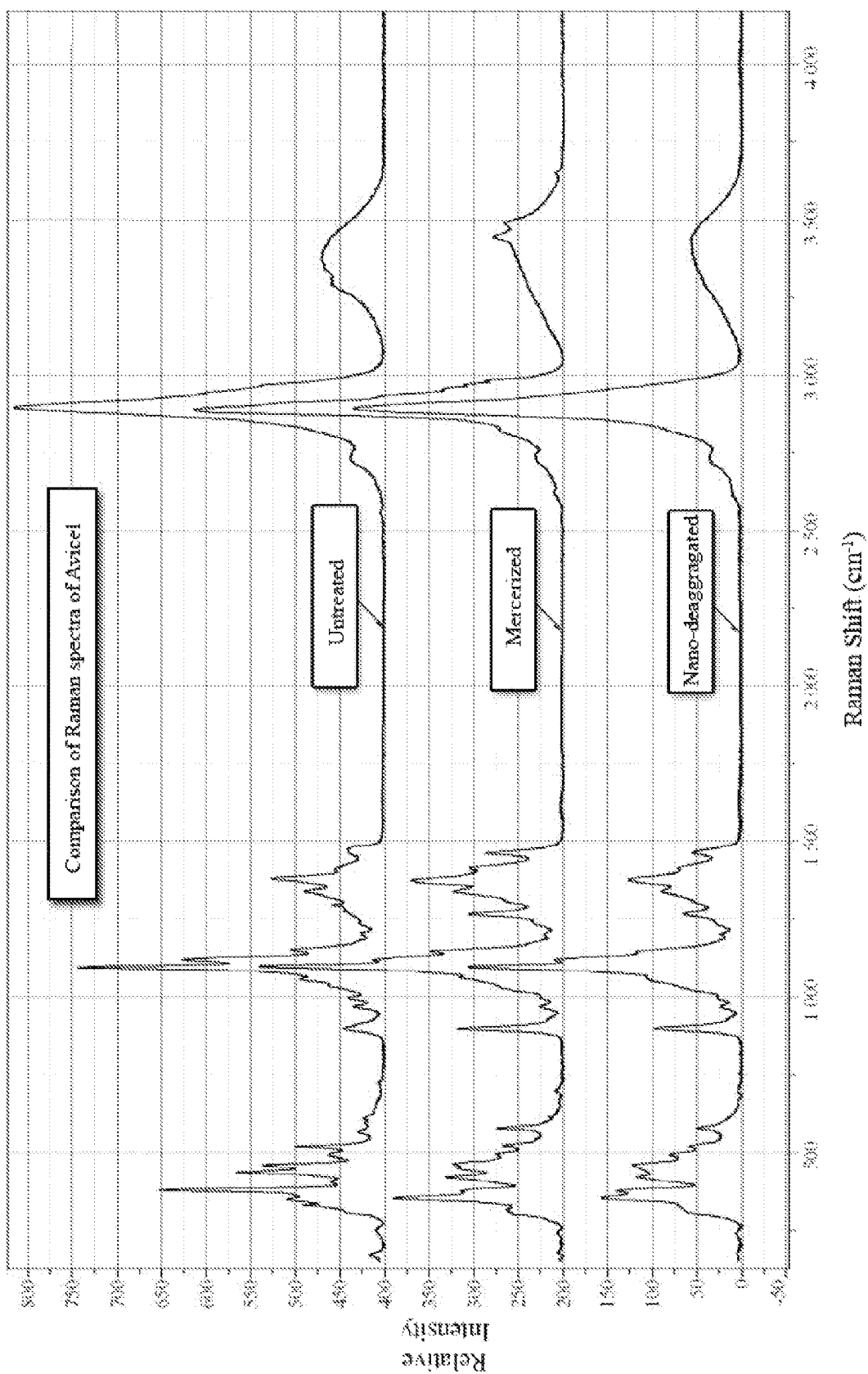
FIGS. 17-20 are Raman spectra of various cellulosic materials before and after pretreatment in accordance with embodiments of the invention.

Additional evidence of the novelty of the state of aggregation of nano-deaggregated cellulose is revealed in the Raman spectra of the three different cellulose samples shown in FIG. 17. FIG. 17 shows Raman spectra of treated, untreated and mercerized Avicel. The spectrum of the untreated Avicel is typical of microcrystalline celluloses, i.e., cellulose I. The spectrum of the mercerized cellulose is also typical of mercerized celluloses or cellulose II. The treated Avicel was prepared in accordance with embodiments of the invention as detailed in the description of treated samples for FIG. 10. For the treated sample, significant changes occur in most regions of the spectra, but particularly significant changes occur in the regions between 200 and 700 cm$^{-1}$, between 1200 and 1500 cm$^{-1}$ and between 3000 and 3800 cm$^{-1}$. The spectrum of the Avicel treated via the process in accordance with embodiments of the invention is distinctly different from either the native Avicel or the mercerized Avicel and is distinctive of the celluloses treated via the process in accordance with embodiments of the invention.

Raman spectra were also obtained for other cellulose source materials. Experimental details are as follows.

Northern Softwood Pulp

The northern softwood pulp treated was a commercial pulp. The treated pulp was processed in accordance with embodiments of the invention, i.e., it was treated with a 1.5 N solution of NaOH in the co-solvent made of 75% ethanol and 25% water. It was then washed with the co-solvent three times then washed with water for three more times.

Figure 18:
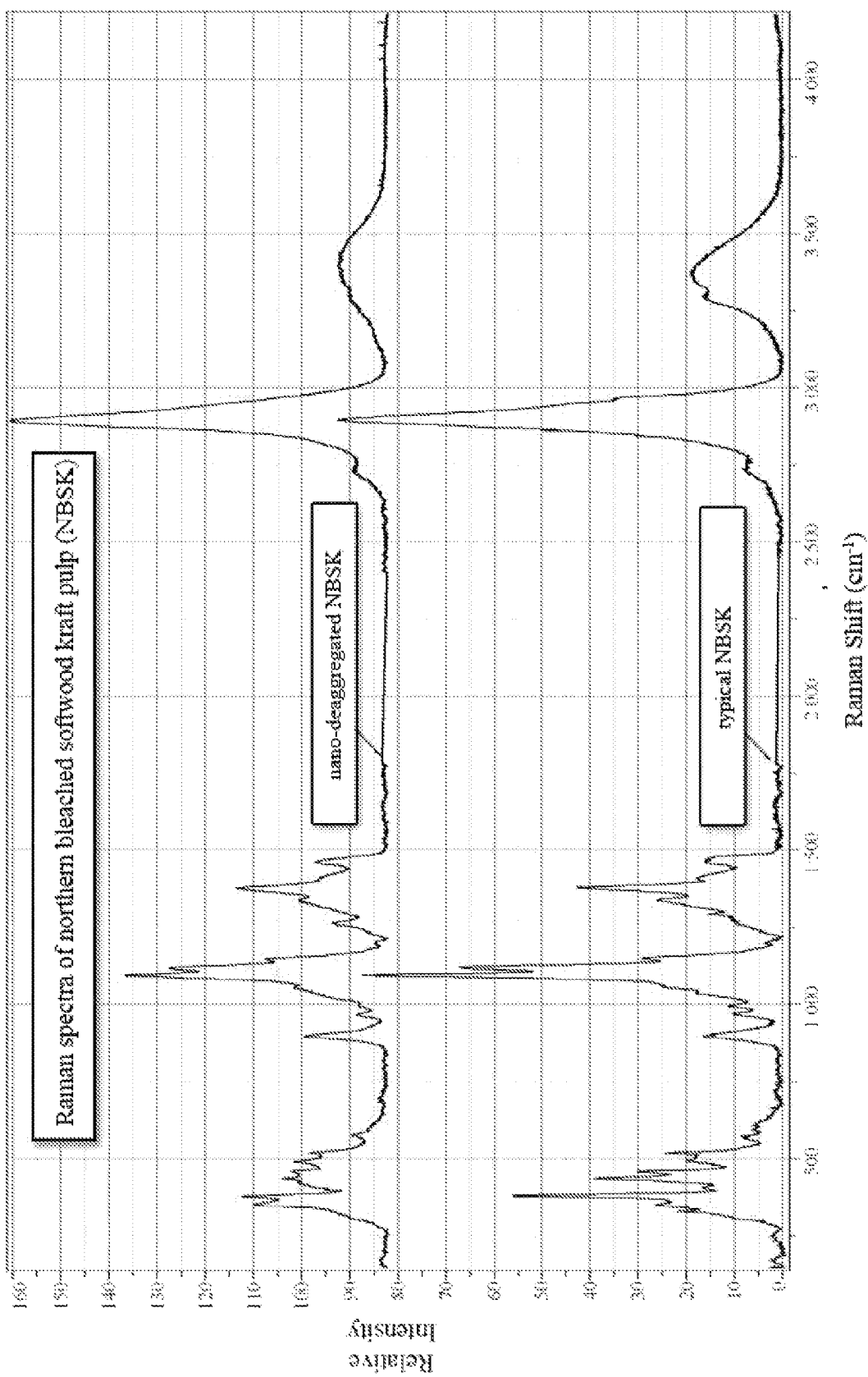

FIG. 18 shows Raman spectra of an untreated northern softwood kraft pulp and one treated via the process in accordance with embodiments of the invention. Again, the most pronounced differences are in the regions between 200 and 700 cm$^{-1}$, between 1200 and 1500 cm$^{-1}$ and between 3000 and 3800 cm$^{-1}$.

Northern Hardwood Pulp

The northern hardwood pulp treated was a commercial pulp. The treatment of the pulp was by the process in accordance with embodiments of the invention, i.e., it was treated with a 1.5 N solution of NaOH in the co-solvent made of 75% ethanol and 25% water. It was then washed with the co-solvent three times then washed with water for three more times.

Figure 19:
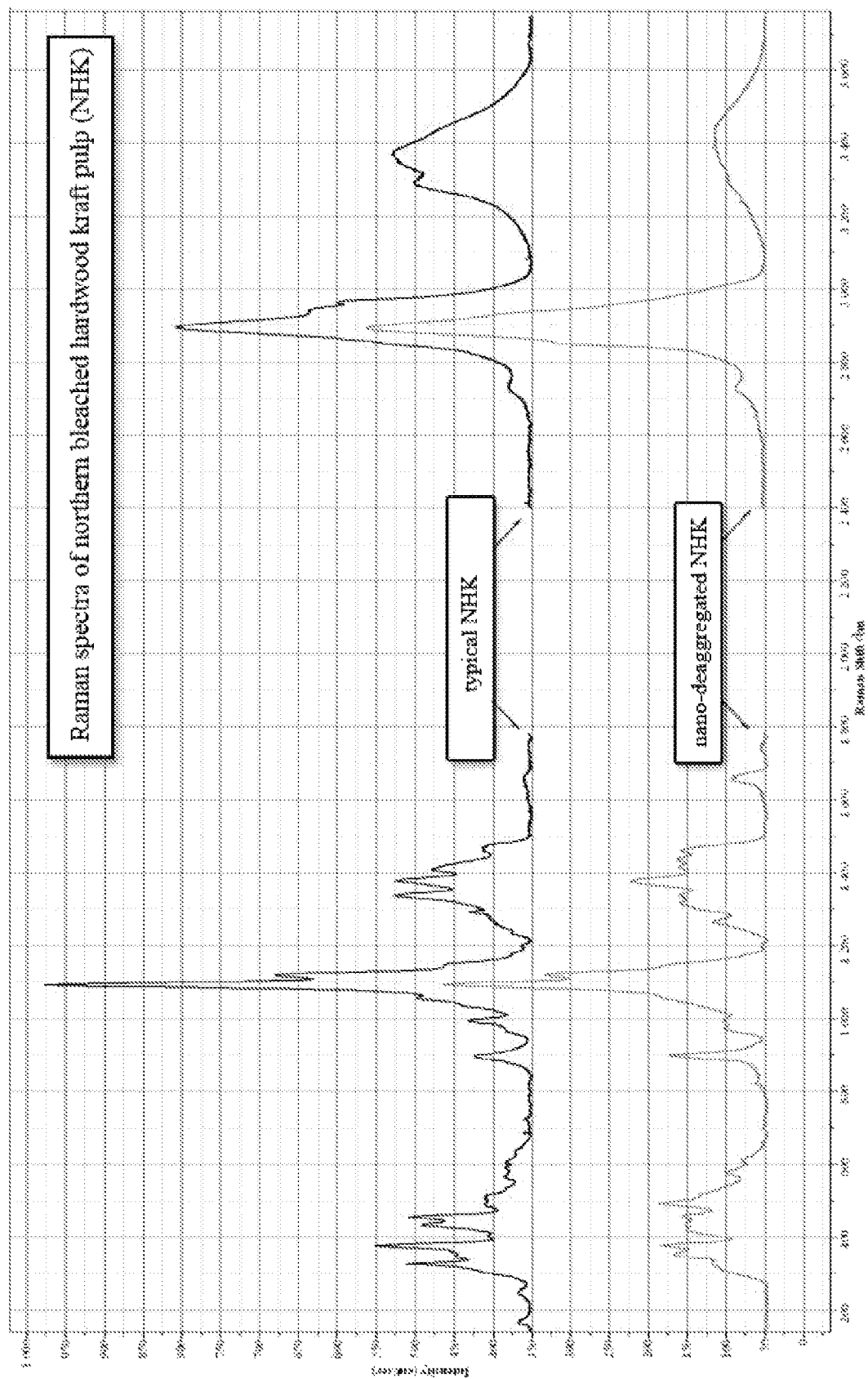

FIG. 19 shows Raman spectra are of an untreated northern hardwood kraft pulp and one treated via the process in accordance with embodiments of the invention. Again, the most pronounced differences are in the regions between 200 and 700 cm$^{-1}$, between 1200 and 1500 cm$^{-1}$ and between 3000 and 3800 cm$^{-1}$ Southern Pine Pulp The southern pine pulp treated was a commercial pulp. The treatment of the pulp was by the process in accordance with embodiments of the invention, i.e., it was treated with a 1.5 N solution of NaOH in the co-solvent made of 75% ethanol and 25% water. It was then washed with the co-solvent three times then washed with water for three more times.

Figure 20:
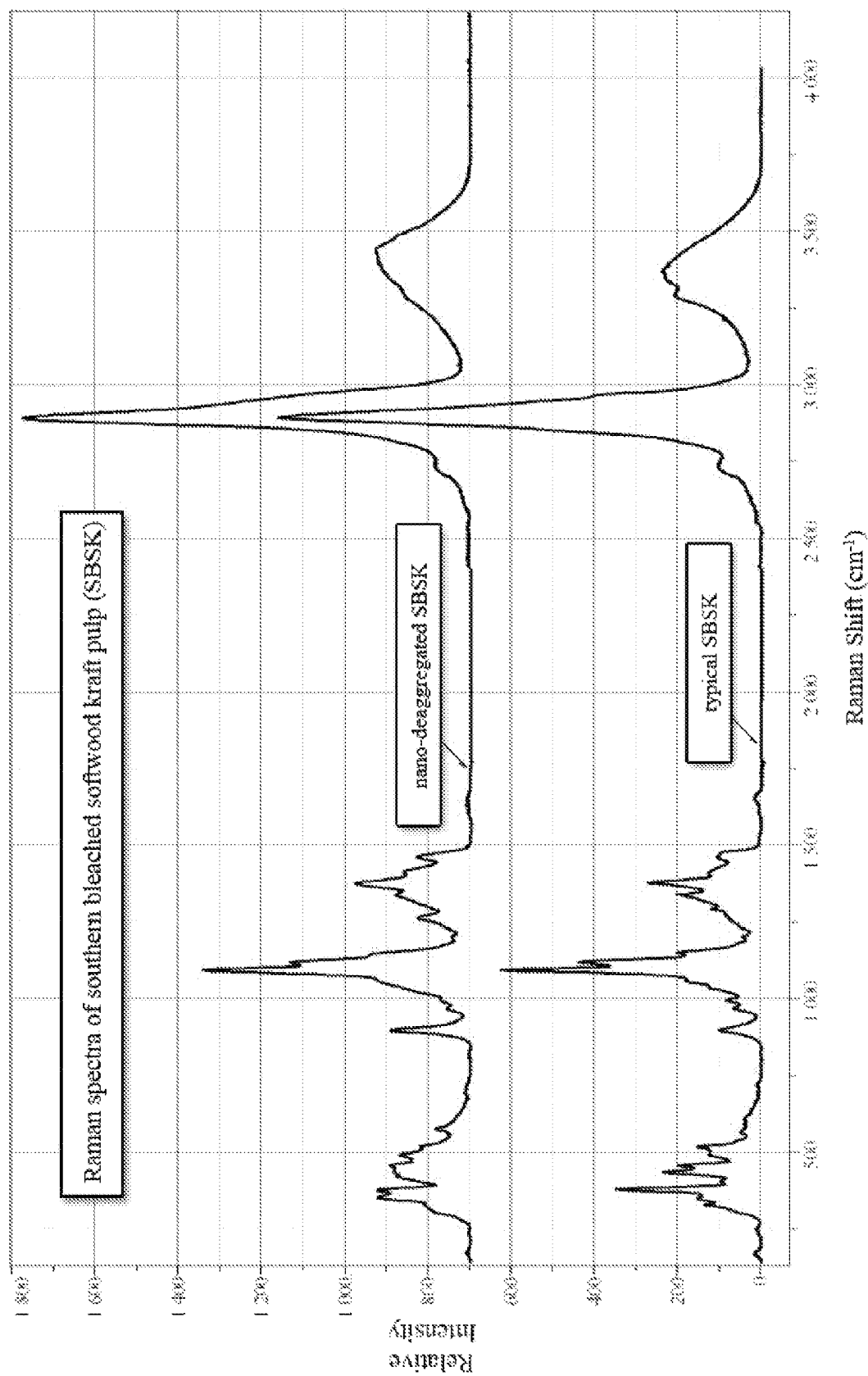

FIG. 20 shows Raman spectra of an untreated southern pine kraft pulp and one treated via the process in accordance with embodiments of the invention. Again, the most pronounced differences are in the regions between 200 and 700 cm$^{-1}$, between 1200 and 1500 cm$^{-1}$ and between 3000 and 3800 cm$^{-1}$ These Raman spectra show that the nano-deaggregated celluloses are quite distinct from celluloses I and II, which are the most common well known forms of cellulose.

NMR Studies

Solid state $^{13}$C NMR spectra of untreated, mercerized and treated Avicel were obtained.

For treated Avicel, Avicel samples were treated as described above for the diffractograms and Raman spectra, i.e., it was treated with a 1.5 N solution of NaOH in the co-solvent made of 75% ethanol and 25% water. It was then washed with the co-solvent three times then washed with water for three more times.

Figure 21:
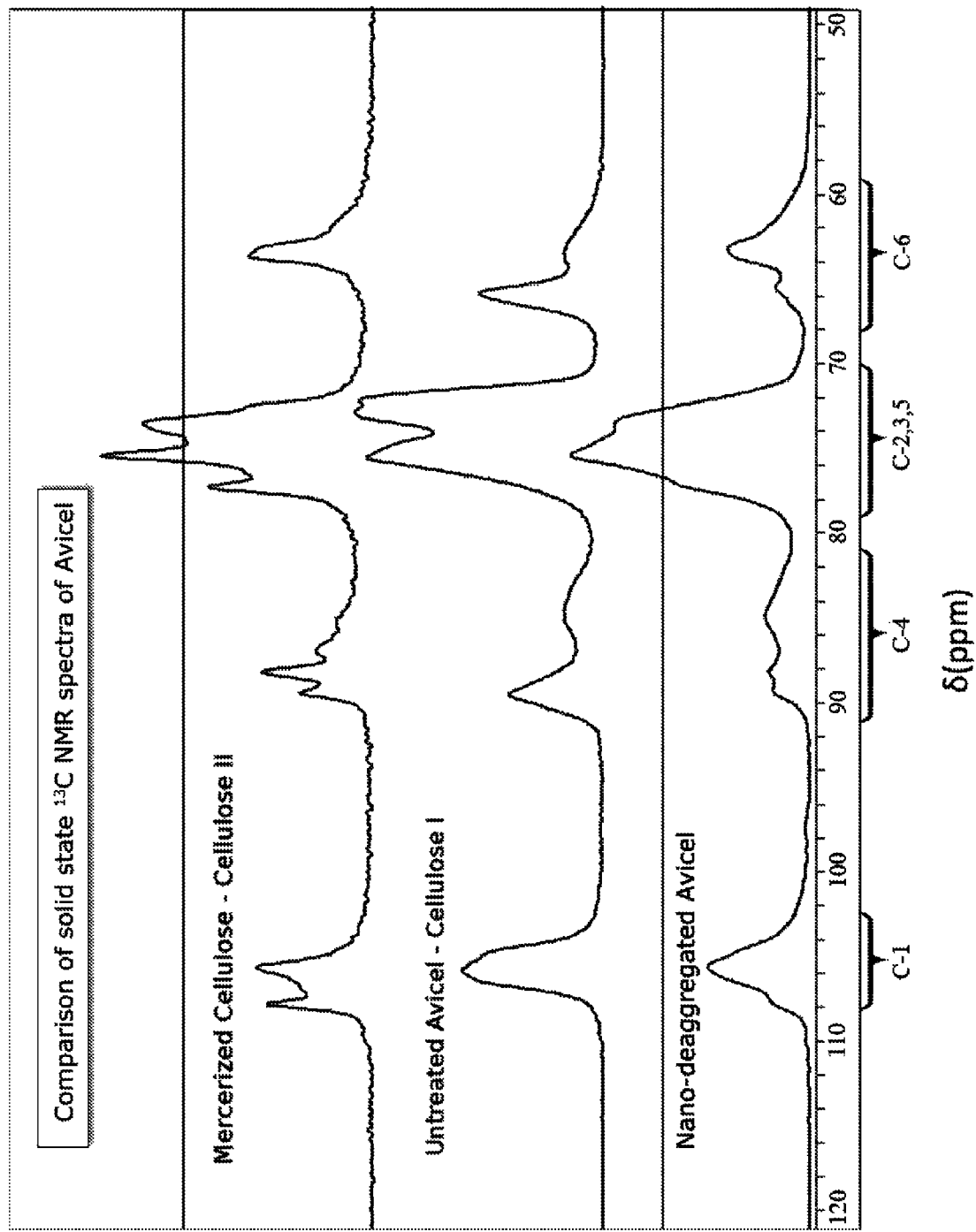
FIG. 21 is a $C^{13}$ solid state NMR of Avicel samples before and after pretreatment in accordance with embodiments of the invention.

FIG. 21 shows solid state 13C NMR spectra of three samples of cellulose prepared from Avicel, which, as noted previously, is a microcrystalline cellulose used as a standard in many studies of cellulose structure. The top spectrum is mercerized Avicel, the middle spectrum is Avicel untreated, the bottom spectrum is Avicel treated by the process in accordance with embodiments of the invention. The treated Avicel shows distinct spectral differences from the cellulose I and II spectra.

The solid state $^{13}$C NMR spectra of the nano-deaggregated cellulose in accordance with embodiments of the invention show very clearly that the nano-deaggregated cellulose is a distinct form of cellulose unlike the two well-known forms.

Micrographic Staining Studies

Untreated and treated Avicel samples were stained with Graff's C stain. This stain is used in microscopic studies of cellulosic fibers. The stain consists of iodine dissolved in a potassium Iodide and chloride solution, and under these conditions, contains large polyiodide ions $I_{13}^-$ and $I_{15}^-$ that are linear chains of 13 or 15 ions that can complex with linearly ordered polysaccharides. These large polyiodide ions usually form blue charge transfer complexes with 1,4 linked polysaccharides most commonly observed in starch.

Figure 22:
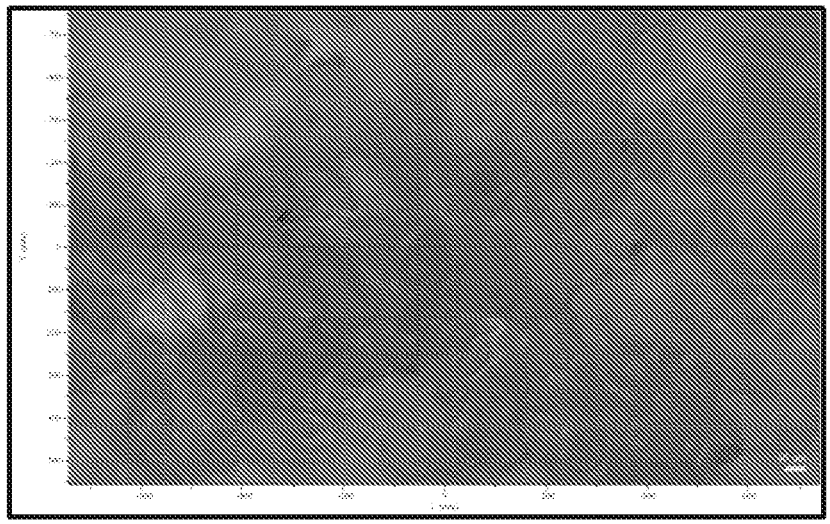
FIG. 22 is a micrograph of microcrystalline cellulose as it occurs after preparation from a high purity dissolving pulp.
Figure 23:
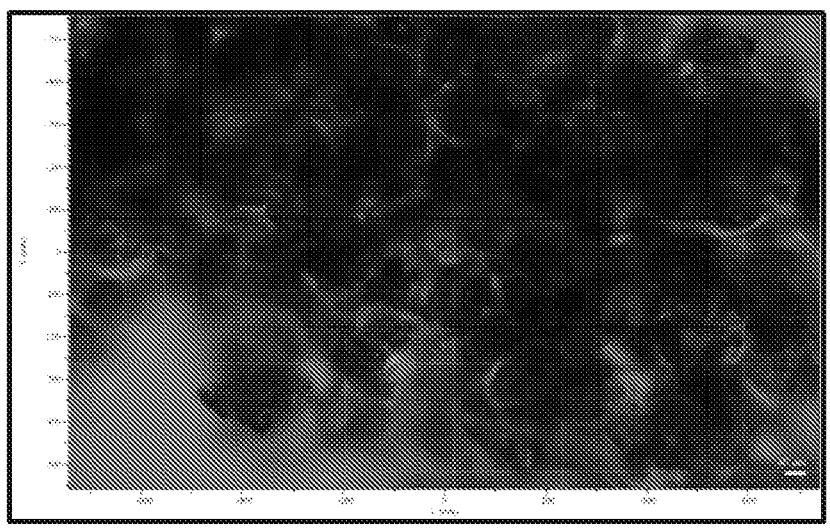
FIG. 23 is a micrograph of this same microcrystalline cellulose which has been processed into nano-deaggregated cellulose in accordance with the invention.

FIGS. 22 and 23 show micrographs of samples of Avicel, which, as explained above, is a microcrystalline cellulose prepared from a high purity dissolving pulp. The sample in FIG. 22 is one of untreated Avicel. The sample in FIG. 23 is Avicel that was treated with the process that results in the novel nano-deaggregated cellulose in accordance with the invention.

The openness of the structure of nano-deaggregated celluloses is demonstrated in FIG. 23 compared to FIG. 22. It is seen that whereas the grains of microcrystalline cellulose, untreated cellulose, in FIG. 22 remain transparent because the stain has affected the surfaces only. On the other hand, the sample in FIG. 23 has become opaque, and appears dark blue or essentially black. In other words, the stained sample shown in FIG. 23 has greater color intensity than the sample shown in FIG. 22. The opaqueness and color intensity of the treated samples of FIG. 23 reflect the porosity of the treated cellulose because the large polyiodide ions that are present in the C stain have been able to penetrate the pores and form the blue complex characteristic of iodine and partially ordered polysaccharides. Thus, the capacity of these large ions to penetrate the novel nano-deaggregated cellulose points to the openness and accessibility at the nanoscale level of the novel nano-deaggregated cellulose.

Accessibility to Enzymes Studies

The openness and accessibility of the deaggregated celluloses to large molecules are also illustrated through exposure to cellulase enzymes. Table 6 shows the results of exposure of two samples of Avicel to enzymes, one Avicel is as it is produced by the manufacturer, and the other is nano-deaggregated cellulose in accordance with embodiments of the invention. The samples were exposed to commercial cellulase enzymes at the dosage recommended by the manufacturer. Exposure of both samples to the enzymes in an appropriately buffered solution was for 30 hours each.

TABLE 6

Conversion of Avicel Samples upon action of cellulase enzymes

| Sample | Initial Weight | Final Weight | % Conversion |
|---|---|---|---|
| Control | 1.000 g | 0.4897 | 51.03 |
| Deaggregated cellulose | 1.002 g | 0.0983 | 90.19 |

As seen in Table 6, nano-deaggregated cellulose, i.e., the sample treated to create the nanoscale disorder of nano-deaggregated cellulose, was nearly completely converted (i.e., at least 90%) to soluble saccharides, while the untreated sample was approximately 50% converted. These results are indicative that the enzyme molecules were able to penetrate nano-deaggregated cellulose sample, while for the control sample the access was limited to surface layers.

Elasticity and Fiber Network Formation Studies

As noted earlier, nano-deaggregated cellulose described herein differs from all other known disordered states of cellulose in that the morphology of the source material is retained. Thus, if the starting material is fibrous, as in a pulp, the individual pulp fibers retain their identity and thus remain suitable for many of the well-established manufacturing procedure that use such fibers as feedstocks. This reality is well illustrated by application of standard handsheet making techniques known in the technology of the pulp and paper industry. Application of this technology also provides a suitable method for demonstrating the enhanced elasticity of nano-deaggregated celluloses.

The handsheet making process begins with a certain amount of pulp fibers slurried in water. The slurry is poured into a vessel with a fine wire mesh at its bottom. As the water flows through the wire, the pulp forms a sheet which is then removed from the wire and pressed and dried. The properties of the sheet formed are determined by the properties of the pulp fibers and reflect these properties. When sheets are formed from pulps treated to induce nano-deaggregated disordered state at the nanoscale level in accordance with the invention, their properties reflect the enhanced elasticity alluded to above. To show the magnitude of the change for nano-deaggregated cellulose, a number of properties have been measured relative to the original pulp starting material. These properties of sheets, produced by the standard method defined by the Technical Association of the Pulp and Paper Industry, are given below.

Caliper: Caliper is the thickness of the sheet after it is dried. The caliper of the hand sheet made from nano-deaggregated cellulose pulp was twice that of the original pulp, indicating that nano-deaggregated cellulose had far higher resilience because the pressure applied in the handset making process is the same for sheets from both pulps.

Void volume: The void volume of the sheet from made from nano-deaggregated cellulose pulp was twice that of the sheet made from the original pulp. This reflects the increased caliper.

Liquid retention: Retention, as measured by porofil liquid retention (g/g of cellulose), for the nano-deaggregated cellulose pulp sheet was twice that of the sheet made from the original pulp.

Gurley porosity: Gurley porosity is a measure of the flow of a measured amount of air through the handsheet. The shorter the time is, the greater the porosity. As measured in seconds, the porosity of the sheet made from original pulp was 7 sec, and 0.8 sec for the sheet from nano-deaggregated cellulose pulp.

Structure of Nano-Deaggregated Cellulose

Figure 24:
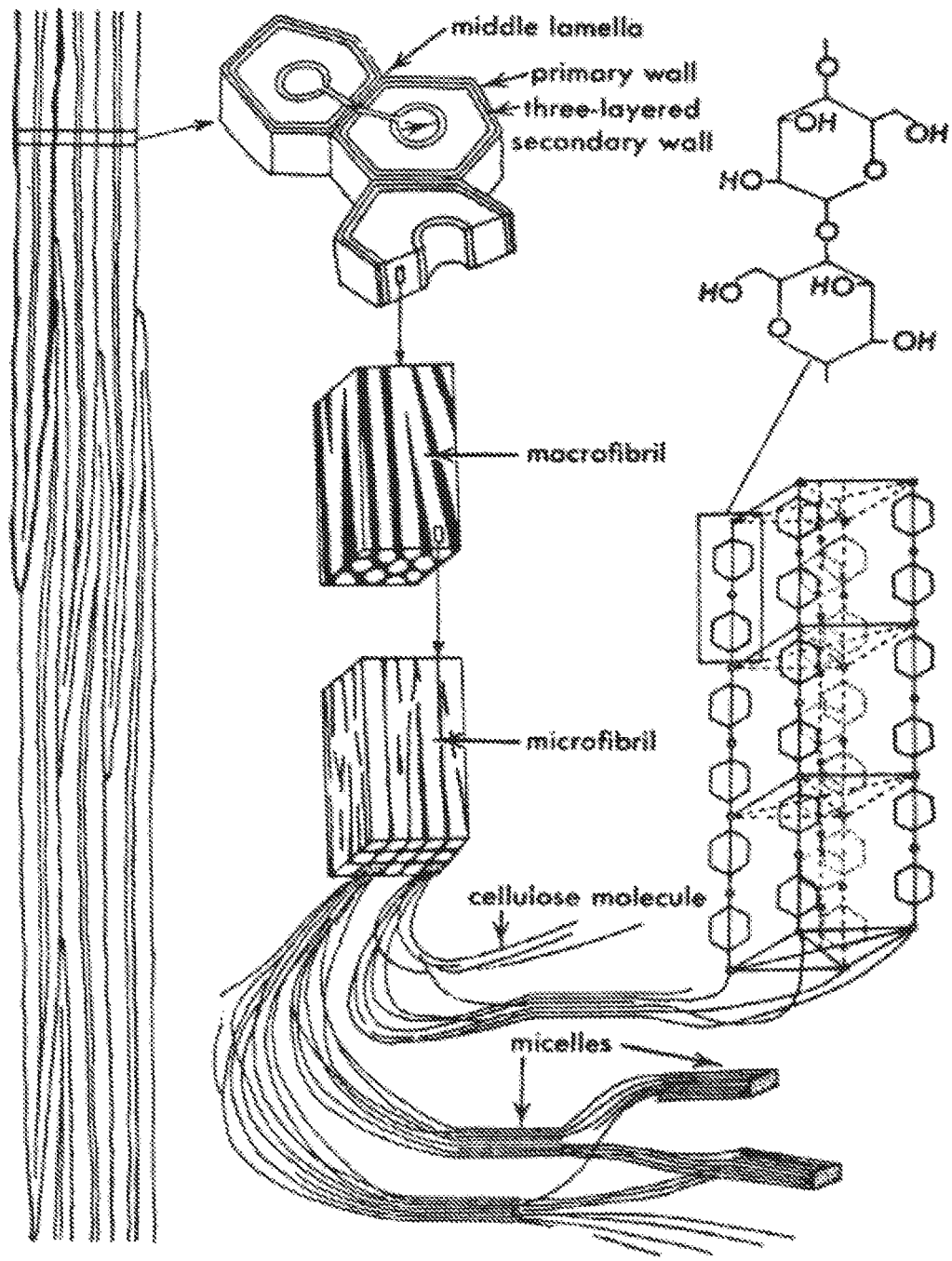
FIG. 24 is a schematic representation of the classical model of cellulose structure.
Figure 25:
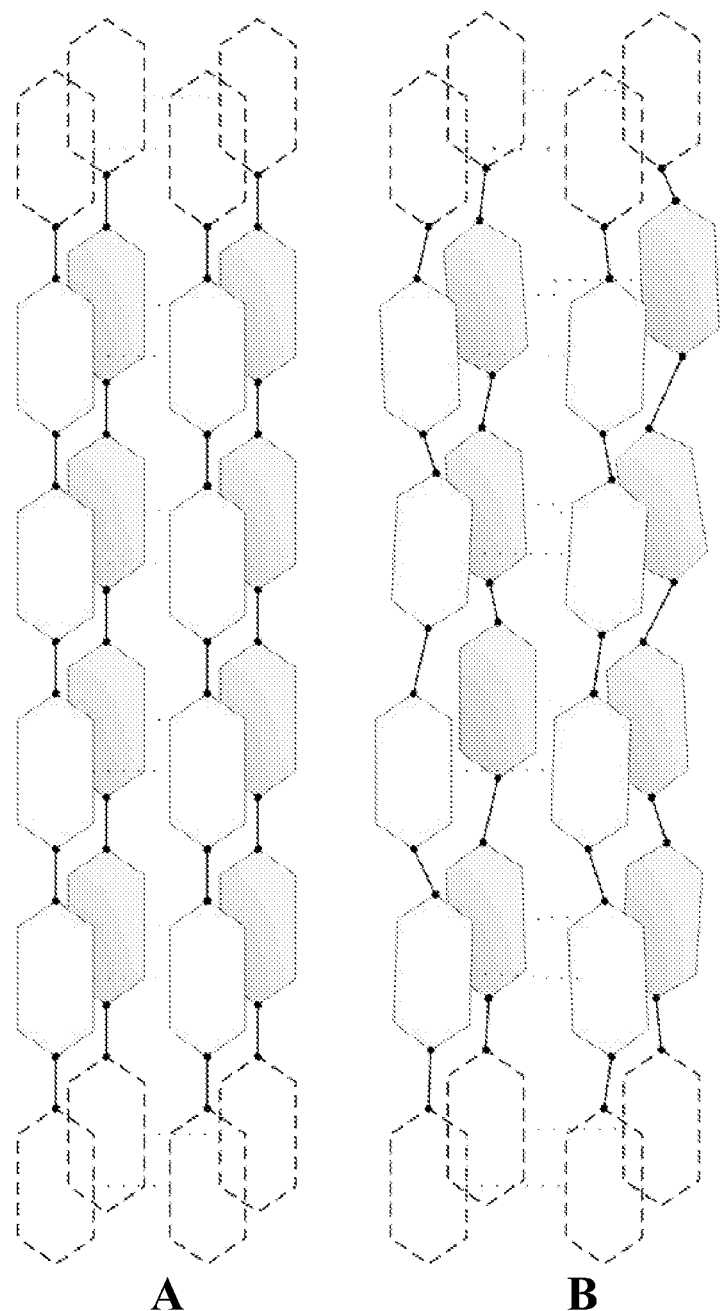
FIG. 25 is a schematic representation comparing cellulose structure before and after pretreatment in accordance with embodiments of the invention.

Reference is now made to FIG. 24 and FIG. 25. FIG. 23 is a schematic representation of a classical model of cellulose structure. FIG. 25A is a schematic representation comparing a classical cellulose structure with FIG. 25B, a representation of nano-deaggregated cellulose in accordance with embodiments of the invention. Without being limited to any particular theory, it is believed that the molecular chains retain their parallel alignment but that there is irregularity in the order within individual chains. As such, the spacings between them is increased and they become more accessible to larger molecules while those in the native state remain tightly organized.

As seen in FIG. 25B, the nano-deaggregated cellulose has a more open structure that allows access and penetrability of other molecules.

In summary, the nano-deaggregated cellulose is a nano-level partially deaggregated cellulose whose structure has internal disorder of the individual cellulosic claims, yet maintains the general parallel spatial relationship of the claims. The nano-deaggregated cellulose demonstrates spectral shifts (i.e., x-ray, Raman, NMR), indicative of nano-scale structural changes, compared to the ordered, "crystalline" cellulose samples from various sources. The shifts are indicative of the internal disorder of the anhydroglucose units within the individual cellulose molecular claims. The nano-deaggregated cellulose is stable in water and generally, in aqueous media, i.e., it does not convert to cellulose II as do amorphous celluloses made by mechanical action when they are immersed in water. Thus, the cellulose in accordance with the principles of the invention is a previously unknown aqueous-stable nano-deaggregated cellulose. As such, the nano-deaggregated cellulose has a greater Graff's C stain color intensity than other celluloses, e.g., cellulose I, and a greater enzymatic hydrolysis to soluble saccharides than other cellulose, e.g., cellulose I or cellulose II. The nano-deaggregated cellulose is also markedly different in structure and properties from amorphous celluloses.

The foregoing description is considered as illustrative only of the principles of the invention. Further, since numerous modifications and changes may readily occur to those skilled in the art, it is not desired to limit the invention to the exact construction and operation shown and described, and accordingly, all suitable modifications and equivalents are considered to fall within the scope of the invention. Various features and advantages of the invention are set forth in the following claims.

All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

REFERENCES

1. "Breaking the Biological Barriers to Cellulosic Ethanol: A Joint Research Agenda" A Research Roadmap Resulting from the Biomass to Biofuels Workshop, December 7-9, 2005, Rockville, Md.: June 2006; DOE/SC-0095.
2. Curtis S. Walseth, "Enzymatic Hydrolysis of Cellulose," Dissertation, Institute of Paper Chemistry, Appleton, Wis. 1948.
3. Bruce E. Dimick, "The Importance of the Structure of Alkali Metal Hydroxide Solutions in Decrystallizing Cellulose I," Dissertation, Institute of Paper Chemistry, Appleton, Wis. 1976.
4. R. Jeffries and J. O. Warwicker, Textile Res, J., 39, 548 (1969).
5. R. H. Atalla and R. Whitmore, "The influence of elevated temperatures of structure in the isolation of native cellulose," J. Polymer Sci. Polymer Lett. 16:601 (1978).
6. R. H. Atalla and S. C. Nagel, "Cellulose: Its regeneration in the native lattice" Science, 185:522 (1974).
7. R. H. Atalla and D. L. VanderHart, "Native cellulose: a composite of two distinct crystalline forms" Science, 223: 283 (1984).
8. R. H. Atalla and U. P. Agarwal, "Raman microprobe evidence for lignin orientation in cell walls of native woody tissue" Science, 227:636 (1985).

The invention claimed is:

1. Nano-deaggregated cellulose, wherein the cellulose is water-stable and is not converted to cellulose II in aqueous media.

2. The nano-deaggregated cellulose of claim 1 having a x-ray pattern as shown in FIGS. 10-16 compared to untreated cellulosic substrates.

3. The nano-deaggregated cellulose of claim 1 having a Raman spectrum as shown in FIGS. 17-20 compared to untreated cellulosic substrates.

4. The nano-deaggregated cellulose of claim 1, further comprising dark opaque grain/cellular stains compared to transparent stains of cellulose I with Graff's C stain.

5. The nano-deaggregated cellulose of claim 1, further comprising a greater enzymatic hydrolysis conversion to soluble saccharides than cellulose I at the same concentration of enzyme.

6. The nano-deaggregated cellulose of claim 5, wherein enzymatic hydrolysis conversion to soluble saccharides is at least 70%.

7. The nano-deaggregated cellulose of claim 5, wherein enzymatic hydrolysis conversion to soluble saccharides is at least 90%.

8. The nano-deaggregated cellulose of claim 1 having NMR spectra as shown in FIG. 21.

9. Nano-deaggregated cellulose having the following properties:
    a) x-ray diffraction peaks at diffraction angle 2Θ different from cellulose I, or cellulose II or amorphous cellulose as shown in FIGS. 10-16;
    b) Raman spectral peaks different from cellulose I or cellulose II as shown in FIGS. 17-20;
    c) NMR spectral peaks different from cellulose I or cellulose II as shown in FIG. 21;
    d) stability in aqueous media;
    e) a greater enzymatic hydrolysis to soluble saccharides than cellulose I or cellulose II at the same concentration of enzyme; and
    f) a greater Graff's C stain color intensity than cellulose I.

10. A composition comprising the nano-deaggregated cellulose of claim 9.

11. A pulp made of nano-deaggregated cellulosic fibers with the composition of claim 10.

12. A pulp made of nano-deaggregated cellulosic fibers with a composition comprising nano-deaggregated cellulose having the following properties:
    a) x-ray diffraction peaks at diffraction angle 2Θ different from cellulose I or cellulose II or amorphous cellulose as shown in FIGS. 10-16;
    b) Raman spectral peaks different from cellulose I or cellulose II as shown in FIGS. 17-20;
    c) NMR spectral peaks different from cellulose I or cellulose II as shown in FIG. 21;
    d) stability in aqueous media;
    e) a greater enzymatic hydrolysis to soluble saccharides than cellulose I or cellulose II at the same concentration of enzyme; and
    f) a greater Graff's C stain color intensity than cellulose I; further comprising, as a handsheet compared to a cellulose I fibrous handsheet, a caliper, void volume and liquid retention which is twice that of the cellulose I hand sheet, and a Gurley porosity of 0.8 sec compared to 7 sec for the cellulose I handsheet.

\* \* \* \* \*